(12) United States Patent
Falo, Jr. et al.

(10) Patent No.: US 10,441,768 B2
(45) Date of Patent: Oct. 15, 2019

(54) BIOACTIVE COMPONENTS CONJUGATED TO SUBSTRATES OF MICRONEEDLE ARRAYS

(71) Applicant: University of Pittsburgh—Of the Commonwealth System of Higher Education, Pittsburgh, PA (US)

(72) Inventors: Louis D. Falo, Jr., Wexford, PA (US); Geza Erdos, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 478 days.

(21) Appl. No.: 15/074,917

(22) Filed: Mar. 18, 2016

(65) Prior Publication Data

US 2016/0271381 A1    Sep. 22, 2016

Related U.S. Application Data

(60) Provisional application No. 62/135,643, filed on Mar. 19, 2015, provisional application No. 62/135,052, filed on Mar. 18, 2015.

(51) Int. Cl.
*A61M 37/00* (2006.01)
*B29C 41/22* (2006.01)
(Continued)

(52) U.S. Cl.
CPC ....... *A61M 37/0015* (2013.01); *B29C 39/025* (2013.01); *B29C 39/123* (2013.01); *B29C 41/22* (2013.01); *B29C 41/34* (2013.01); *A61M 2037/0023* (2013.01); *A61M 2037/0046* (2013.01); *A61M 2037/0053* (2013.01); *A61M 2037/0061* (2013.01); *A61M 2202/0007* (2013.01); *A61M 2202/0057* (2013.01); (Continued)

(58) Field of Classification Search
CPC .... A61M 37/00154; A61M 2202/0007; A61M 2037/0046; B29L 2031/756; B29L 2031/7544; B29K 2995/006
See application file for complete search history.

(56) References Cited

U.S. PATENT DOCUMENTS 5,312,456 A     5/1994  Reed
5,658,515 A     8/1997  Lee et al.
(Continued)

FOREIGN PATENT DOCUMENTS

CN          147590 A        3/2004
JP       2005-35945         2/2005
(Continued)

OTHER PUBLICATIONS

Xie et al., "Toll-like receptor 2 mediates invasion via activating NF-κB in MDA-MB-231 breast cancer cells," *Biochemical and Biophysical Research Communications* 379(4): 1027-1032, 2009.
(Continued)

*Primary Examiner* — Carlos A Azpuru
(74) *Attorney, Agent, or Firm* — Klarquist Sparkman, LLP

(57) ABSTRACT

Microneedle arrays and methods of forming the same can include one or more bioactive components bonded to a biocompatible material such that the one or more bioactive components are cleavable in vivo to release the bioactive component from the biocompatible material.

64 Claims, 24 Drawing Sheets

(51) Int. Cl.
 *B29C 41/34* (2006.01)
 *B29C 39/02* (2006.01)
 *B29C 39/12* (2006.01)
 *B29K 1/00* (2006.01)
 *B29L 31/00* (2006.01)

(52) U.S. Cl.
 CPC .... *B29K 2001/08* (2013.01); *B29K 2995/006* (2013.01); *B29L 2031/753* (2013.01); *B29L 2031/756* (2013.01); *B29L 2031/7544* (2013.01)

(56) References Cited

U.S. PATENT DOCUMENTS

| | | |
|---|---|---|
| 6,331,266 B1 | 12/2001 | Powell et al. |
| 6,451,240 B1 | 9/2002 | Sherman et al. |
| 6,511,463 B1 | 1/2003 | Wood et al. |
| 6,565,871 B2 | 5/2003 | Roser et al. |
| 6,611,707 B1 | 8/2003 | Prausnitz et al. |
| 6,623,707 B1 | 9/2003 | Addiego et al. |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,743,211 B1 | 6/2004 | Prausnitz et al. |
| 6,767,211 B2 | 7/2004 | Hall et al. |
| 6,881,203 B2 | 4/2005 | Delmore et al. |
| 6,899,838 B2 | 5/2005 | Lastovich |
| 6,908,453 B2 | 6/2005 | Fleming et al. |
| 6,924,087 B2 | 8/2005 | Yeshurun et al. |
| 6,931,277 B1 | 8/2005 | Yuzhakov et al. |
| 7,052,268 B2 | 5/2006 | Powell et al. |
| 7,132,054 B1 | 11/2006 | Kravitz et al. |
| 7,211,062 B2 | 5/2007 | Kwon |
| 7,226,439 B2 | 6/2007 | Prausnitz et al. |
| 7,285,113 B2 | 10/2007 | Yeshurun |
| 7,315,758 B2 | 1/2008 | Kwiatkowski et al. |
| 7,316,665 B2 | 1/2008 | Laurent et al. |
| 7,332,197 B2 | 2/2008 | Wood et al. |
| 7,364,568 B2 | 4/2008 | Angel et al. |
| 7,416,541 B2 | 8/2008 | Yuzhakov et al. |
| 7,429,333 B2 | 9/2008 | Chiou et al. |
| 7,497,980 B2 | 3/2009 | Xu et al. |
| 7,560,036 B2 | 7/2009 | Golubovic-Liakopoulos et al. |
| 7,578,954 B2 | 8/2009 | Gartstein et al. |
| 7,588,552 B2 | 9/2009 | Yeshurun et al. |
| 7,591,806 B2 | 9/2009 | Xu |
| 7,648,484 B2 | 1/2010 | Yeshurun et al. |
| 7,651,475 B2 | 1/2010 | Angel et al. |
| 7,658,728 B2 | 2/2010 | Yuzhakov |
| 7,699,819 B2 | 4/2010 | Yeung et al. |
| 7,731,968 B2 | 6/2010 | Mikszta et al. |
| D619,245 S | 7/2010 | Moga et al. |
| 7,753,888 B2 | 7/2010 | Mukerjee et al. |
| 7,763,203 B2 | 7/2010 | Arias et al. |
| 7,785,301 B2 | 8/2010 | Yuzhakov |
| 7,846,488 B2 | 12/2010 | Johnson et al. |
| 7,850,657 B2 | 12/2010 | Yeshurun et al. |
| D638,534 S | 5/2011 | Moga et al. |
| 8,052,633 B2 | 11/2011 | Kendall |
| 8,057,842 B2 | 11/2011 | Choi et al. |
| 8,062,573 B2 | 11/2011 | Kwon |
| 8,062,835 B2 | 11/2011 | Tomono |
| 8,088,321 B2 | 1/2012 | Ferguson et al. |
| 8,101,114 B2 | 1/2012 | Park et al. |
| 8,137,736 B2 | 3/2012 | Zhu et al. |
| 8,162,901 B2 | 4/2012 | Gonnelli et al. |
| 8,167,852 B2 | 5/2012 | Quan et al. |
| 8,172,815 B2 | 5/2012 | Down et al. |
| 8,192,787 B2 | 6/2012 | Kirby |
| 8,216,190 B2 | 7/2012 | Gartstein et al. |
| 8,236,368 B2 | 8/2012 | Jung et al. |
| 8,246,582 B2 | 8/2012 | Angel et al. |
| 8,246,893 B2 | 8/2012 | Ferguson et al. |
| 8,250,729 B2 | 8/2012 | Lee et al. |
| 8,257,324 B2 | 9/2012 | Prausnitz et al. |
| 8,267,889 B2 | 9/2012 | Cantor et al. |
| 8,328,757 B2 | 12/2012 | Beebe et al. |
| 8,353,861 B2 | 1/2013 | Tobinaga et al. |
| 8,354,033 B2 | 1/2013 | Scholten et al. |
| 8,361,037 B2 | 1/2013 | Gonnelli |
| 8,366,677 B2 | 2/2013 | Kaspar et al. |
| 8,376,984 B2 | 2/2013 | James |
| 8,402,629 B2 | 3/2013 | Lee et al. |
| 8,414,548 B2 | 4/2013 | Yuzhakov |
| 8,414,959 B2 | 4/2013 | Hye-Ok et al. |
| 8,419,708 B2 | 4/2013 | Tokumoto et al. |
| 8,444,622 B2 | 5/2013 | Eckhoff et al. |
| 8,449,807 B2 | 5/2013 | Ferguson et al. |
| 8,454,844 B2 | 6/2013 | Yeshurun et al. |
| 8,491,534 B2 | 7/2013 | Takada |
| 8,506,530 B2 | 8/2013 | Laermer et al. |
| 8,506,980 B2 | 8/2013 | Takada |
| 8,545,741 B2 | 10/2013 | Jung et al. |
| 8,551,391 B2 | 10/2013 | Chang et al. |
| 8,554,317 B2 | 10/2013 | Duan |
| 8,560,059 B2 | 10/2013 | Hoarau et al. |
| 8,579,862 B2 | 11/2013 | Kobayashi et al. |
| 8,603,384 B2 | 12/2013 | Luttge et al. |
| 8,636,696 B2 | 1/2014 | Ross et al. |
| 8,637,136 B2 | 1/2014 | Ferguson et al. |
| 8,671,544 B2 | 3/2014 | Xu et al. |
| 8,696,637 B2 | 4/2014 | Ross |
| 8,696,638 B2 | 4/2014 | Terahara et al. |
| 8,708,966 B2 | 4/2014 | Allen et al. |
| 8,734,697 B2 | 5/2014 | Chen et al. |
| 8,741,377 B2 | 6/2014 | Choi et al. |
| 8,747,362 B2 | 6/2014 | Terahara et al. |
| 8,758,298 B2 | 6/2014 | Cantor et al. |
| 8,771,781 B2 | 7/2014 | Tokumoto et al. |
| 8,784,368 B2 | 7/2014 | Eckhoff et al. |
| 8,784,373 B2 | 7/2014 | Gharib et al. |
| 8,784,383 B2 | 7/2014 | Cole et al. |
| 8,784,384 B2 | 7/2014 | Boyden et al. |
| 8,784,385 B2 | 7/2014 | Boyden et al. |
| 8,784,860 B2 | 7/2014 | Falotico et al. |
| 8,785,400 B2 | 7/2014 | Levetan et al. |
| 8,788,037 B2 | 7/2014 | Della Rocca et al. |
| 8,788,211 B2 | 7/2014 | Boyden et al. |
| 8,788,212 B2 | 7/2014 | Boyden et al. |
| 8,790,257 B2 | 7/2014 | Libbus et al. |
| 8,790,259 B2 | 7/2014 | Katra et al. |
| 8,790,658 B2 | 7/2014 | Cigarini et al. |
| 8,791,062 B2 | 7/2014 | Hsu et al. |
| 8,791,107 B2 | 7/2014 | Chang et al. |
| 8,793,075 B2 | 8/2014 | Boyden et al. |
| 8,795,174 B2 | 8/2014 | Manicka et al. |
| 8,795,201 B2 | 8/2014 | Escutia et al. |
| 8,795,230 B2 | 8/2014 | Schoonmaker et al. |
| 8,795,234 B2 | 8/2014 | Kadamus et al. |
| 8,795,259 B2 | 8/2014 | Beebe et al. |
| 8,796,436 B2 | 8/2014 | Manoharan et al. |
| 8,798,722 B2 | 8/2014 | Rylander et al. |
| 8,798,932 B2 | 8/2014 | Boyden et al. |
| 8,798,933 B2 | 8/2014 | Boyden et al. |
| 8,821,446 B2 | 9/2014 | Trautman et al. |
| 8,821,779 B2 | 9/2014 | Ferguson et al. |
| 8,834,423 B2 | 9/2014 | Falo, Jr. |
| 2002/0082543 A1 | 6/2002 | Park et al. |
| 2002/0193729 A1 | 12/2002 | Cormier et al. |
| 2002/0198509 A1 | 12/2002 | Mikszta et al. |
| 2004/0058882 A1 | 3/2004 | Eriksson et al. |
| 2005/0013221 A1 | 1/2005 | Sato |
| 2005/0019918 A1 | 1/2005 | Sumimoto et al. |
| 2005/0049549 A1 | 3/2005 | Wong et al. |
| 2005/0065463 A1 | 3/2005 | Tobinaga et al. |
| 2005/0089553 A1 | 4/2005 | Cormier et al. |
| 2005/0251088 A1 | 11/2005 | Kwon |
| 2007/0161964 A1 | 7/2007 | Yuzhakov |
| 2007/0260201 A1 | 11/2007 | Prausnitz et al. |
| 2008/0009763 A1 | 1/2008 | Chiou et al. |
| 2008/0208134 A1 | 8/2008 | Tomono |
| 2008/0213461 A1 | 9/2008 | Gill et al. |
| 2008/0221532 A1 | 9/2008 | Ogawa |

(56) References Cited

U.S. PATENT DOCUMENTS

| | | | |
|---|---|---|---|
| 2008/0269658 A1* | 10/2008 | Vinton | A61M 35/00 602/48 |
| 2008/0269685 A1 | 10/2008 | Singh et al. | |
| 2009/0054842 A1 | 2/2009 | Yeshurun et al. | |
| 2009/0232855 A1 | 9/2009 | Kwon et al. | |
| 2010/0042137 A1 | 2/2010 | Oronsky et al. | |
| 2010/0228203 A1 | 9/2010 | Quan et al. | |
| 2011/0046575 A1 | 2/2011 | Takada | |
| 2011/0098651 A1* | 4/2011 | Falo, Jr. | A61M 37/0015 604/173 |
| 2011/0172605 A1 | 7/2011 | Berenschot et al. | |
| 2011/0230736 A1 | 9/2011 | Tepper et al. | |
| 2012/0078189 A1 | 3/2012 | Ogawa et al. | |
| 2012/0123341 A1 | 5/2012 | Birchall et al. | |
| 2012/0265145 A1 | 10/2012 | Mefti et al. | |
| 2012/0283695 A1 | 11/2012 | Chen et al. | |
| 2013/0072902 A1 | 3/2013 | Takada et al. | |
| 2013/0096532 A1 | 4/2013 | Ozel et al. | |
| 2014/0066843 A1 | 3/2014 | Zhang et al. | |
| 2014/0142492 A1 | 5/2014 | Jung et al. | |
| 2014/0142541 A1* | 5/2014 | Yan | A61K 47/38 604/506 |
| 2015/0030642 A1 | 1/2015 | Wu et al. | |
| 2015/0126923 A1 | 5/2015 | Falo, Jr. | |

FOREIGN PATENT DOCUMENTS

| | | |
|---|---|---|
| JP | 2011-224332 | 11/2011 |
| WO | WO 98/00194 | 1/1998 |
| WO | WO 2004/000389 | 12/2003 |
| WO | WO 2008/091602 | 7/2008 |
| WO | WO 2009-004995 | 1/2009 |
| WO | WO 2009/009004 | 1/2009 |
| WO | WO 2009/040548 | 4/2009 |
| WO | WO 2009/081122 | 7/2009 |
| WO | WO 2009/094394 | 7/2009 |
| WO | WO 2010/022252 | 2/2010 |
| WO | WO 2010/071918 | 7/2010 |
| WO | WO 2010/141377 | 12/2010 |
| WO | WO 2012/054582 | 4/2012 |
| WO | WO 2012/153266 | 11/2012 |
| WO | 2013166162 A1 * | 11/2013 |
| WO | WO 2013/166162 | 11/2013 |
| WO | WO 2014/012147 | 1/2014 |
| WO | 2015048777 A1 * | 4/2015 |
| WO | WO 2015/048777 | 4/2015 |
| WO | WO 2015/149031 | 10/2015 |

OTHER PUBLICATIONS

European Search Report dated Mar. 10, 2016 by the European Patent Office, for EPC App. No. 13784192.0, 14 pages.
Examination Report, dated Dec. 16, 2016, for corresponding Australian Patent Application No. 2013256348, 3 pages.
Filiz et al., "Micromilling of microbarbs for medical implants" *Internationall Journal of Machine Tools and Manufacture* 48(3): 459-472, 2008.
International Preliminary Report on Patentability dated Sep. 16, 2013 by the Korean Intellectual Property Office, acting as ISA for PCT application No. PCT/US2013/039084, 8 pages.
International Preliminary Report on Patentability dated Jan. 14, 2016 by the Australian Patent Office, acting as ISA for PCT application No. PCT/US2015/059556, 6 pages.
International Preliminary Report on Patentability dated Jul. 5, 2016 by the Korean Intellectual Property Office, acting as ISA for PCT application No. PCT/US2016/02374, 15 pages.
International Search Report and Written Opinion dated Sep. 16, 2013 by the Korean Intellectual Property Office, acting as ISA for PCT application No. PCT/US2013/039084, 10 pages.
International Search Report and Written Opinion dated Jan. 14, 2016 by the Australian Patent Office, acting as ISA for PCT App. No. PCT/US2015/059556, 11 pages.
International Search Report and Written Opinion dated Jul. 5, 2016 by the Korean Intellectual Property Office, acting as ISA for PCT application No. PCT/US2016/02374, 18 pages.
Lee et al., "Dissolving microneedles for transdermal drug delivery." *Biomaterials* 29(13): 2113-2124, 2008.
Office Action, dated Jan. 25, 2017, for corresponding Japanese Patent Application No. 2015-510434, with English language translation, 11 pages.
Office Action, dated Apr. 14, 2017, in corresponding Chinese Patent Application No. 201380031604.6, with English-language translation, 9 pages.
Office Action, dated Sep. 14, 2017, for corresponding Japanese Patent Application No. 2015-510434, with English language translation, 11 pages.
Office Action, dated Sep. 26, 2017, for corresponding Mexican Patent Application No. MX/a/2014/013234, no English language translation, 4 pages.
Office Action, dated Oct. 31, 2017, in corresponding Chinese Patent Application No. 201380031604.6, with English-language translation, 18 pages.
Office Action, dated Dec. 27, 2017, for corresponding Taiwanese Application No. 2017-78229, no English language translation, 5 pages.
International Search Report and Written Opinion dated Jan. 10, 2017 by the Australian Patent Office, acting as ISA for PCT application No. PCT/US2016/057363, 11 pages.
Ma et al., "Poly (I: C) inhibits melanoma metastasis and enhances chemerin expression and NK cell recruitment via a RIG-like helicase innate immune/MAVS-dependent mechanism," In C38. Pulmonary and Systemic Inflammation, American Thoracic Society, pp. A4165-A4165, 2013.
Filiz et al., "Micromilling of microbarbs for medical implants," *International Journal of Machine Tools and Manufacture* 48(3-4): 459-472, 2008.
Kim et al., "Microneedles for drug and vaccine delivery," *Advanced Drug Deliver Reviews* 64(14): 1547-1568, 2012.
Khodadust et al., "Development of poly (I: C) modified doxorubicin loaded magnetic dendrirner nanoparticles for targeted combination therapy," *Biomedicine & Pharmacotherapy* 68(8): 979-987, 2014.
Shiozuka et al., "Transdermal delivery of adriamycin to transplanted Ehrlich ascites tumor in mice," *Pharmaceutics* 5(3): 385-391, 2013.

* cited by examiner

FIG. 15
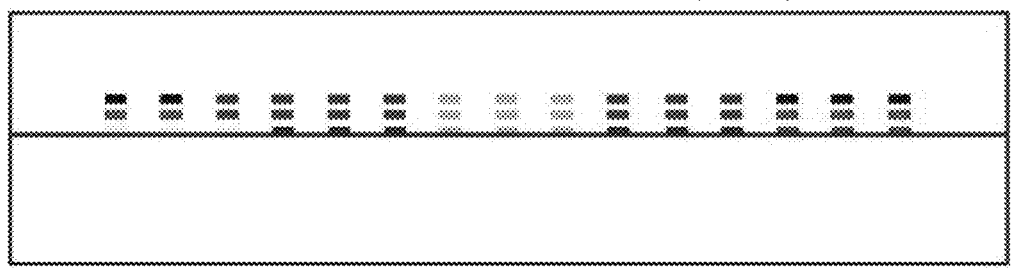
Cross-section of the CMC-solid with layers of active components and interleaving CMC layers
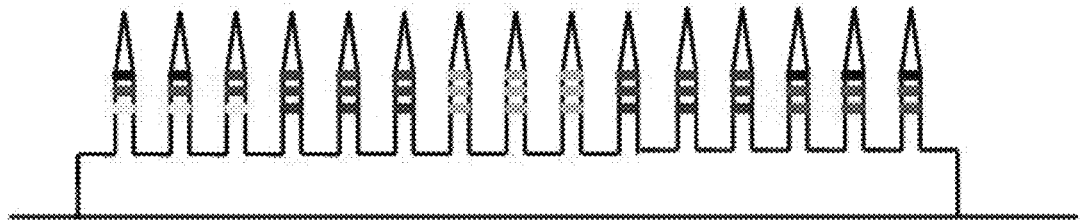
Cross-section of finished MNA-device after the micro-milling process

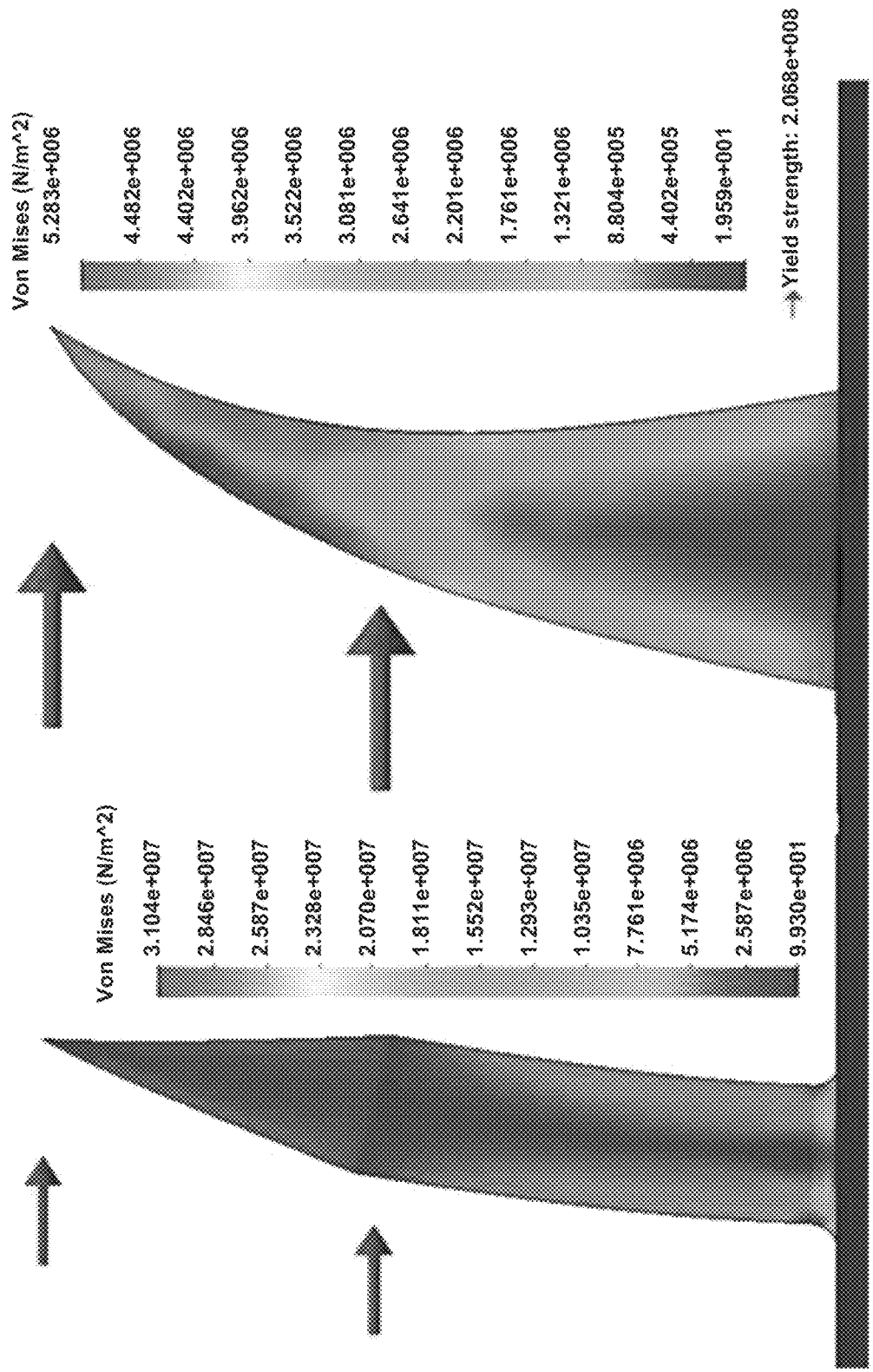

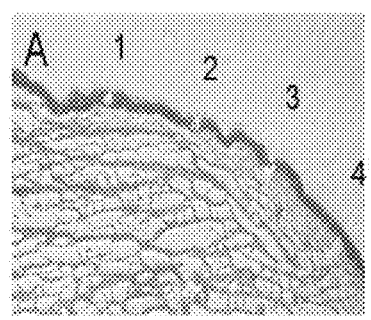
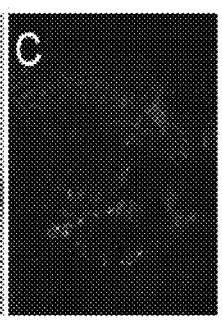
FIG. 25A  FIG. 25B  FIG. 25C
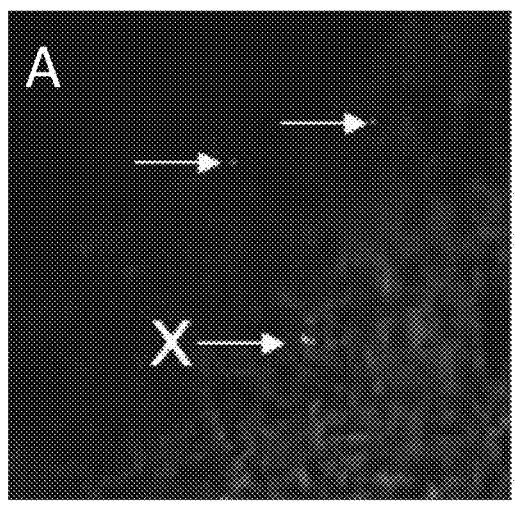
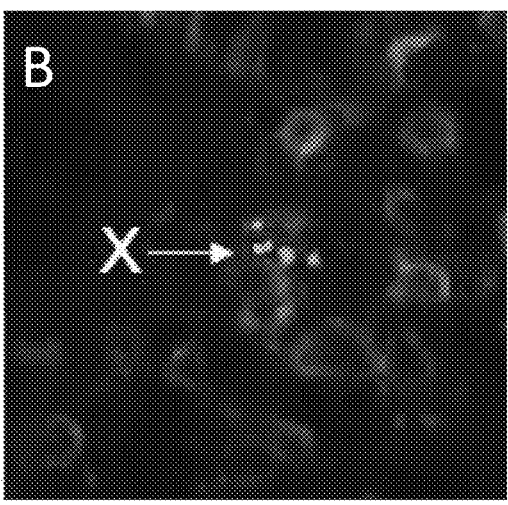
FIG. 26A  FIG. 26B
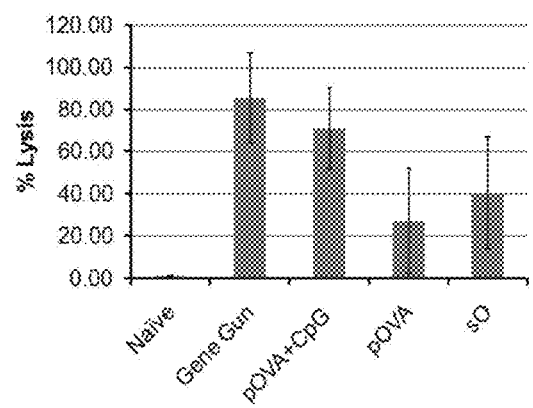
FIG. 27

BIOACTIVE COMPONENTS CONJUGATED TO SUBSTRATES OF MICRONEEDLE ARRAYS

CROSS REFERENCE TO RELATED APPLICATIONS

This application claims the benefit of U.S. Provisional Application No. 62/135,052, filed Mar. 18, 2015; and U.S. Provisional Application No. 62/135,643, filed Mar. 19, 2015; each of which is herein incorporated by reference in its entirety.

ACKNOWLEDGMENT OF GOVERNMENT SUPPORT

This invention was made with government support under grant number NIH P50 CA121973 awarded by the National Institutes of Health. The government has certain rights in the invention.

FIELD

The disclosure pertains to systems and methods for transdermal drug delivery, and, in particular, to systems and methods for making and using dissolvable microneedle arrays.

BACKGROUND

The remarkable physical barrier function of the skin poses a significant challenge to transdermal drug delivery. To address this challenge, a variety of microneedle-array based drug delivery devices have been developed. For example, one conventional method employs solid or hollow microneedles arrays with no active component. Such microneedle arrays can pre-condition the skin by piercing the stratum corneum and the upper layer of epidermis to enhance percutaneous drug penetration prior to topical application of a biologic-carrier or a traditional patch. This method has been shown to significantly increase the skin's permeability; however, this method provides only limited ability to control the dosage and quantity of delivered drugs or vaccine.

Another conventional method uses solid microneedles that are surface-coated with a drug. Although this method provides somewhat better dosage control, it greatly limits the quantity of drug delivered. This shortcoming has limited the widespread application of this approach and precludes, for example, the simultaneous delivery of optimal quantities of combinations of antigens and/or adjuvant in vaccine applications.

Another conventional method involves using hollow microneedles attached to a reservoir of biologics. The syringe needle-type characteristics of these arrays can significantly increase the speed and precision of delivery, as well as the quantity of the delivered cargo. However, complex fabrication procedures and specialized application settings limit the applicability of such reservoir-based microneedle arrays.

Yet another conventional method involves using solid microneedle arrays that are biodegradable and dissolvable. Current fabrication approaches for dissolvable polymer-based microneedles generally use microcasting processes. However, such conventional processes are limited in the active components that can be embedded into the array and are also wasteful in that they require that the active components be homogenously embedded in the microneedles and their support structures.

Accordingly, although transdermal delivery of biologics using microneedle-array based devices offers attractive theoretical advantages over prevailing oral and needle-based drug delivery methods, considerable practical limitations exist with conventional delivery systems and methods.

SUMMARY

The systems and methods disclosed herein include cutaneous delivery platforms based on dissolvable microneedle arrays that can provide efficient, precise, and reproducible delivery of biologically active molecules to human skin. The microneedle array delivery platforms can be used to deliver a broad range of bioactive components to a patient.

In one embodiment, a dissolvable microneedle array for transdermal insertion into a patient is provided that includes a substrate comprising a biocompatible material that forms base portion and a plurality of microneedles extending from the base portion and one or more bioactive components conjugated to the biocompatible material. The one or more bioactive components are cleavable in vivo to release the bioactive component from the biocompatible material, or the bioactive component retains function when conjugated to the biocompatible material.

The one or more bioactive components can be covalently bonded to the biocompatible material, such as by a disulfide bond. The microneedle array of claim 1, wherein the biocompatible material can be carboxymethylcellulose. The one or more bioactive components can be cleavable in vivo by an enzyme, and/or in response to pH, temperature, or both. The one or more bioactive components can be the same or different bioactive components, and one, or both, of the bioactive components can be conjugated to the biocompatible material. The at least two different bioactive components are selected from the group consisting of a chemotherapeutic agent, an adjuvant, and a chemo attractant for a cancer chemo immunotherapy application. In other embodiments, the bioactive component can include an antigen and an adjuvant for a vaccine application, and/or can include at least one viral vector, which can comprise in some cases an adenovector.

In some examples, the one or more bioactive components comprise Doxorubicin, such as in an amount from about 1 to 1000 μg for chemotherapy. In some examples, the microneedle arrays can provide the one or more bioactive components in a higher concentration in the plurality of microneedles than in the base portion. In other examples, substantially all of the one or more bioactive components are located in the plurality of microneedles so that the base portion is substantially formed without any bioactive components contained therein. The one or more bioactive components can be locally concentrated in the plurality of microneedles so that the one or more bioactive components are generally present only in an upper half of respective microneedles in the microneedle array. Each microneedle can include a plurality of layers of the biocompatible material.

A method of fabricating a microneedle array is also provide. The method includes applying a first solution of a dissoluble biocompatible material having one or more bioactive components conjugated to the dissoluble biocompatible material therein to a microneedle array production mold; applying a second solution of the dissoluble biocompatible material that does not contain one or more active components to the microneedle array production mold; and drying the first and second solutions to form a solid microneedle array that comprises a base portion and a plurality of microneedles that extend from the base portion. The one or more active components can be substantially concentrated in the plurality of microneedles, and the one or more bioactive components can be covalently bonded to the dissoluble biocompatible material such that the conjugated bioactive components are cleavable in vivo to release the bioactive component from the biocompatible material.

In another embodiment, a dissolvable microneedle array for transdermal insertion into a patient is provided. The array includes a substrate comprising a biocompatible material that forms base portion and a plurality of microneedles extending from the base portion, and a first bioactive component conjugated to the biocompatible material. The bioactive component is Doxorubicin and the Doxorubicin is cleavable in vivo to release it from the biocompatible material, or the Doxorubicin retains function when conjugated to the biocompatible material.

In some embodiments, the Doxorubicin is covalently bonded to the biocompatible material (e.g., CMC), such as by a disulfide bond. The Doxorubicin can be cleavable in vivo by an enzyme, and/or cleavable in vivo in response to pH, temperature, or both. The amount of Doxorubicin ranges from about 1 to 1000 µg for chemotherapy.

In other embodiments, the array also includes a second bioactive component, such as one selected from the group consisting of Poly-IC or Poly-ICLC. The second bioactive component can also conjugated to the biocompatible material or it can be mixed into the biocompatible material.

The foregoing and other objects, features, and advantages of the disclosed embodiments will become more apparent from the following detailed description, which proceeds with reference to the accompanying figures.

BRIEF DESCRIPTION OF THE DRAWINGS

FIG. 15 is a schematic illustration of exemplary microneedle arrays fabricated in a spatially controlled manner.

FIG. 23 illustrates a finite elements model of microneedle deflections for pillar type microneedles (left) and pyramidal type microneedles (right).

FIGS. 25A-25C illustrate the effectiveness of microneedle arrays in penetrating skin explants.

FIGS. 26A and 26B illustrate in vivo delivery of particulates to the skin draining lymph nodes of microneedle array immunized mice.

FIG. 27 is a bar graph showing immunogenicity of microneedle delivered model antigens.

DETAILED DESCRIPTION

Figure 1:
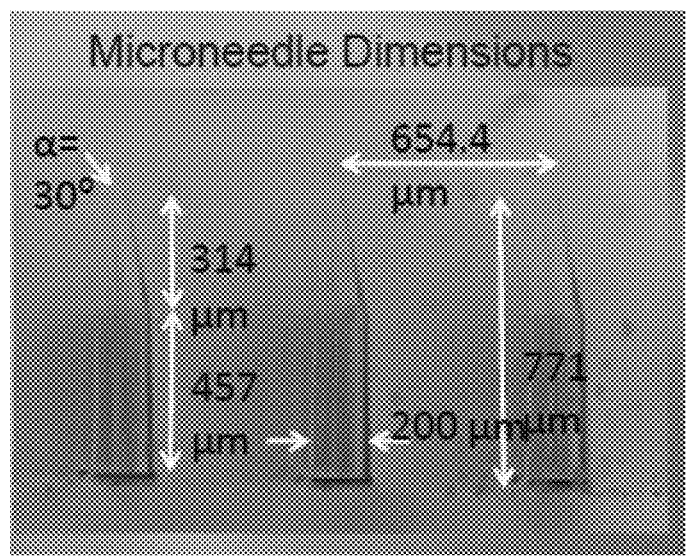
FIG. 1 illustrates exemplary microneedles and their dimensions.

The following description is exemplary in nature and is not intended to limit the scope, applicability, or configuration of the disclosed embodiments in any way. Various changes to the described embodiment may be made in the function and arrangement of the elements described herein without departing from the scope of the disclosure.

As used in this application and in the claims, the singular forms "a," "an," and "the" include the plural forms unless the context clearly dictates otherwise. Additionally, the term "includes" means "comprises." As used herein, the terms "biologic," "active component," "bioactive component," "bioactive material," or "cargo" refer to pharmaceutically active agents, such as analgesic agents, anesthetic agents, anti-asthmatic agents, antibiotics, anti-depressant agents, antidiabetic agents, anti-fungal agents, anti-hypertensive agents, anti-inflammatory agents, anti-neoplastic agents, anxiolytic agents, enzymatically active agents, nucleic acid constructs, immunostimulating agents, immunosuppressive agents, vaccines, and the like. The bioactive material can comprise dissoluble materials, insoluble but dispersible materials, natural or formulated macro, micro and nano particulates, and/or mixtures of two or more of dissoluble, dispersible insoluble materials and natural and/or formulated macro, micro and nano particulates.

As used herein, the term "pre-formed" means that a structure or element is made, constructed, and/or formed into a particular shape or configuration prior to use. Accordingly, the shape or configuration of a pre-formed microneedle array is the shape or configuration of that microneedle array prior to insertion of one or more of the microneedles of the microneedle array into the patient.

As used herein, the term "conjugate" means two or more moieties directly or indirectly coupled together. Two entities are conjugated when under physiological conditions of pH, ionic strength and osmotic potential, the majority of the entities are associated with each other at equilibrium, such as due to the presence of a convalent bond. Covalent linkage may be by any of a variety of chemical linking and cross-linking agents including, for example, homobifunctional or heterobifunctional crosslinking reagents, many of which are commercially available (see, e.g., Pierce Chemical Co. or Sigma Chemical Co.). Linking or crosslinking can be achieved by any of a variety of chemistries well known in the art including, for example, activated polyethylene glycols, aldehydes, isocyanates, maleimides and the like. Linking or cross-linking can also be achieved using physical methods, such as irradiation, for example gamma irradiation or ultraviolet (UV) irradiation. For example, a first moiety may be covalently or noncovalently (e.g., electrostatically) coupled to a second moiety. Indirect attachment is possible, such as by using a "linker" (a molecule or group of atoms positioned between two moieties).

As used herein, "cancer" means a malignant neoplasm that has undergone characteristic anaplasia with loss of differentiation, increase rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived. Cancer includes, but is not limited to, solid tumors.

As used herein, "tumor" means an abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

As used herein, "chemotherapeutic agents" means any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Chemotherapeutic agents include those known by those skilled in the art, including but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol. Rapamycin has also been used as a chemotherapeutic.

As used herein, "therapeutically effective dose" means a dose sufficient to prevent advancement, or to cause regression of a disease, or which is capable of relieving symptoms caused by a disease, such as pain.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Tip-Loaded Microneedle Arrays

Dissolvable microneedle arrays enable efficient and safe drug and vaccine delivery to the skin and mucosal surfaces. However, inefficient drug delivery can result from the homogenous nature of conventional microneedle array fabrication. Although the drugs or other cargo that is to be delivered to the patient are generally incorporated into the entire microneedle array matrix, in practice only the microneedles enter the skin and therefore, only cargo contained in the volume of the individual needles is deliverable. Accordingly, the vast majority of the drugs or other cargo that is localized in the non-needle components (e.g., the supporting structure of the array) is never delivered to the patient and is generally discarded as waste.

Figure 2:
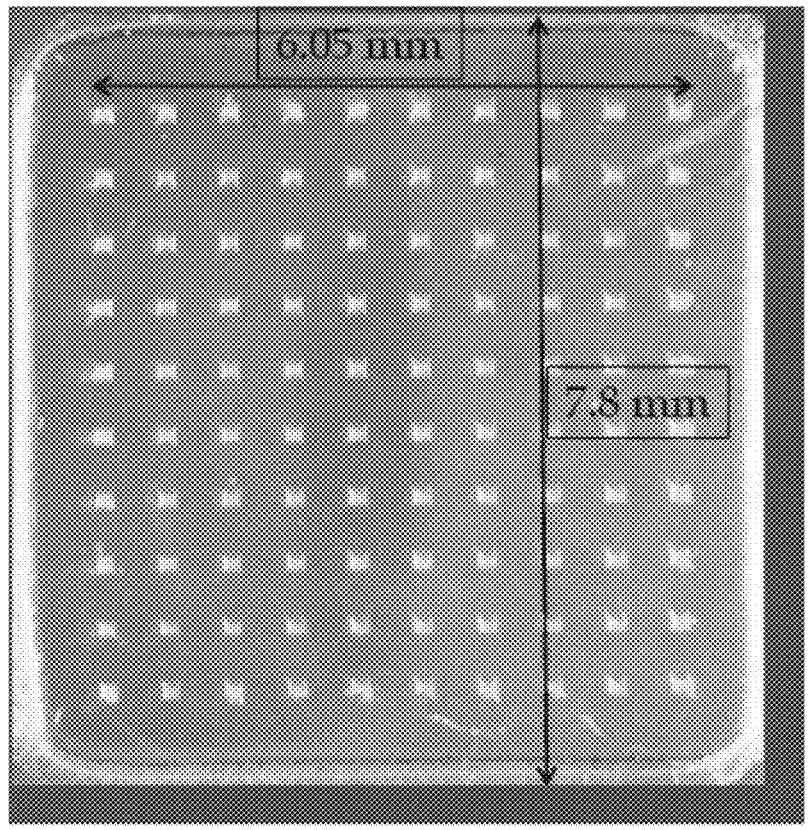
FIG. 2 illustrates an exemplary microneedle array and its dimensions.
Figure 3A:
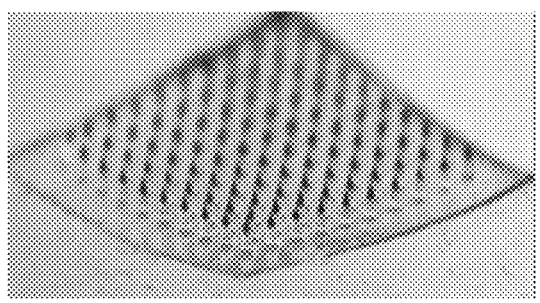
FIGS. 3A and 3B illustrate exemplary microneedles with tip-loaded active components.
Figure 3B:
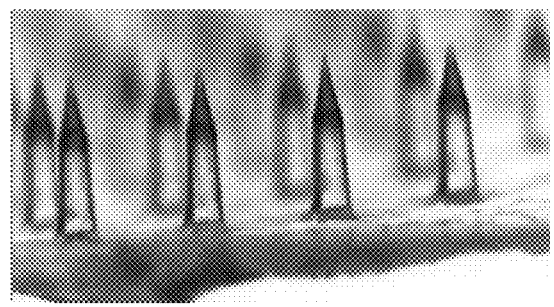
Figure 4A:
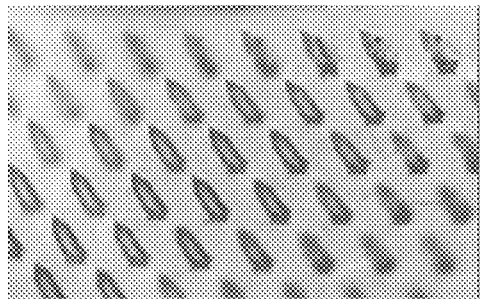
FIGS. 4A and 4B illustrate exemplary microneedles with tip-loaded active components.
Figure 4B:
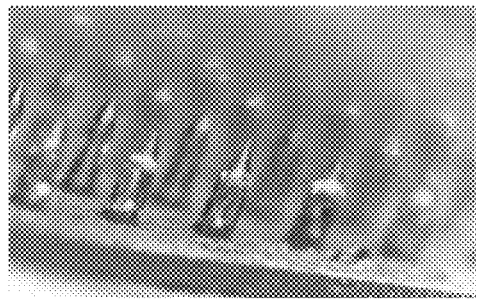

FIGS. 1 and 2 illustrate exemplary dimensions of microneedles and microneedle arrays. Based on the illustrative sizes shown in FIGS. 1 and 2, a microneedle array that comprises an active component homogenously distributed throughout the array exhibits active component waste of greater than 40 percent. For example, if the entire area of the array is 61 mm$^2$ and the microneedle array area is 36 mm$^2$, then the percent utilization of the active component is less than 60 percent. Although the dimensions reflected in FIGS. 1 and 2 illustrate a particular size array and shape of microneedles, it should be understood that similar waste is present in any other size microneedle array in which the active component is homogenously distributed throughout the array, regardless of the size of the array or the shape of the microneedles involved.

The systems and methods described herein provide novel microneedle array fabrication technology that utilizes a fully-dissolvable microneedle array substrate and unique microneedle geometries that enable effective delivery of a broad range of active components, including a broad range of protein and/or small molecule medicines and vaccines.

As described in more detail herein, in some embodiments, this technology can also uniquely enable the simultaneous co-delivery of multiple chemically distinct agents for polyfunctional drug delivery. Examples of the utility of these devices include, for example, (1) simultaneous delivery of multiple antigens and adjuvants to generate a polyvalent immune response relevant to infectious disease prevention and cancer therapy, (2) co-delivery of chemotherapeutic agents, immune stimulators, adjuvants, and antigens to enable simultaneous adjunct tumor therapies, and (3) localized skin delivery of multiple therapeutic agents without systemic exposure for the treatment of a wide variety of skin diseases.

In some embodiments, the systems and method disclosed herein relate to a novel fabrication technology that enables various active components to be incorporated into the needle tips. Thus, by localizing the active components in this manner, the remainder of the microneedle array volume can be prepared using less expensive matrix material that is non-active and generally regarded as safe. The net result is greatly improved efficiency of drug delivery based on (1) reduced waste of non-deliverable active components incorporated into the non-needle portions of the microneedle array, and (2) higher drug concentration in the skin penetrating needle tips. This technological advance results in dramatically improved economic feasibility proportional to the cost of drug cargo, and increased effective cargo delivery capacity per needle of these novel microneedle arrays.

FIGS. 3A, 3B, 4A, and 4B illustrate various embodiments of microneedle arrays wherein the active component is concentrated in the microneedle tips of the respective arrays. Thus, in contrast to conventional microneedle arrays, the active component is not present at even concentration throughout the microneedle array since there is little or no active component present in the supporting base structure. In addition, in some embodiments (as shown, for example, in FIGS. 3A, 3B, 4A, and 4B), not only is there little or no active component in the supporting structures, the location of the active component is concentrated in the upper half of the individual microneedles in the array.

Figure 5A:
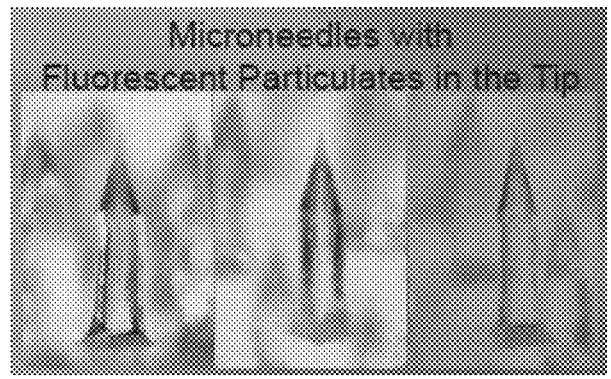
FIGS. 5A and 5B illustrate exemplary microneedles with tip-loaded active components.
Figure 5B:
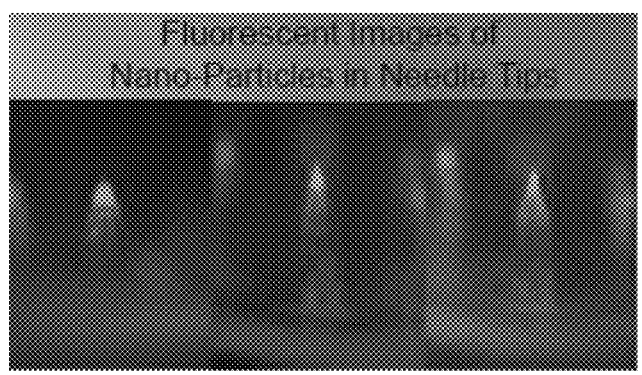

FIGS. 5A and 5B illustrate exemplary images of microneedles of a microneedle array that contains active component concentrated in the upper half of the individual microneedles. The active component is illustrated as fluorescent particles that are concentrated in the tip of the microneedle, with the tip being defined by an area of the microneedle that extends from a base portion in a narrowing and/or tapered manner. The base portion, in turn, extends from the supporting structure of the array.

Figure 6A:
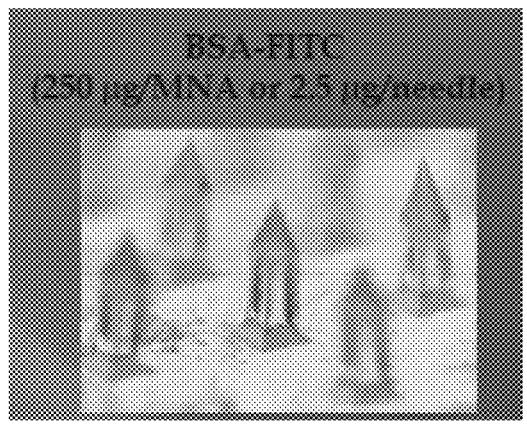
FIGS. 6A and 6B illustrate exemplary microneedles with tip-loaded active components.
Figure 6B:
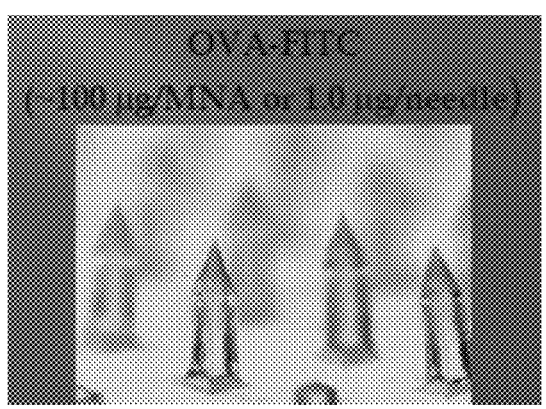

FIGS. 6A and 6B illustrate additional exemplary images of microneedles of microneedle arrays that contain active components concentrated in the upper half of the individual microneedles. In FIG. 6A, the active component, which is concentrated in the tip of the microneedles, is BSA-FITC. In FIG. 6B, the active component, which is also concentrated in the tip of the microneedles, is OVA-FITC.

As noted above, in some embodiments, individual microneedles can comprise active components only in the upper half of the microneedle. In other embodiments, individual microneedles can comprise active components only in the tips or in a narrowing portion near the tip of the microneedle. In still other embodiments, individual needles can comprise active components throughout the entire microneedle portion that extends from the supporting structure.

The following embodiments describe various exemplary methods for fabricating microneedle arrays with one or more active component concentrated in the upper halves and/or tips of microneedles in respective microneedle arrays.

Microneedle Arrays Fabricated by Sequential Micro-Molding and Spin-Drying Methods The following steps describe an exemplary method of fabricating microneedle arrays using sequential micro-molding and spin-drying. Active components/cargo can be prepared at a desired useful concentration in a compatible solvent. As described herein, the solvents of the active component(s) can be cargo specific and can comprise a broad range of liquids, including for example, water, organic polar, and/or apolar liquids. Examples of active components are discussed in more detail below and various information about those active components, including tested and maximum loading capacity of various microneedle arrays are also discussed in more detail below.

If desired, multiple loading cycles can be performed to achieve higher active cargo loads as necessary for specific applications. In addition, multiple active cargos can be loaded in a single loading cycle as a complex solution, or as single solutions in multiple cycles (e.g., repeating the loading cycle described below) as per specific cargo-compatibility requirements of individual cargos. Also, particulate cargos (including those with nano- and micro-sized geometries) can be prepared as suspensions at the desired particle number/volume density.

Example 1 a) As described in more detail below in the micromilling embodiments, an active cargo's working stock solution/suspension can be applied to the surface of microneedle array production molds at, for example, about 40 µl per cm² surface area.

b) The microneedle array production molds with active cargo(s) can be centrifuged at 4500 rpm for 10 minutes to fill the microneedle array production molds needles with the working cargo stock.

c) The excess cargo solution/suspension can be removed and the surface of the microneedle array production molds, washed with 100 µl phosphate buffer saline (PBS) per cm² mold-surface area, or with the solvent used for the preparation of the active cargo's working stock.

d) The microneedle array production molds containing the active cargo stock solution/suspension in the needle's cavity can be spin-dried at 3500 rpm for 30 minutes at the required temperature with continues purging gas flow through the centrifuge at 0-50 L/min to facilitate concentration of the drying active cargo(s) in the needle-tips. The purging gas can be introduced into the centrifuge chamber through tubular inlets. Moisture content can be reduced using a dehumidifier tempered to the required temperature with recirculation into the centrifuge chamber. The purging gas can be air, nitrogen, carbon dioxide or another inert or active gas as required for specific cargo(s). The flow rate is measured by flow-meters and controlled by a circulating pump device.

e) 100 µl 20% CMC90 hydrogel in $H_2O$ can be added to the surface microneedle array production molds' per cm² microneedle array production molds-area to load the structural component of the microneedle array device.

f) The microneedle array production molds can be centrifuged at 4500 rpm for 10 min at the required temperature without purging gas exchange in the centrifuge chamber to fill up the microneedle array production molds needle cavities with the CMC90 hydrogel. This can be followed by a 30 min incubation period to enable rehydration of the active cargo(s) previously deposited in the microneedle array tips.

g) The microneedle array production molds can centrifuged at 3500 rpm for 3 hours or longer at the required temperature with 0-50 L/min constant purging gas flow through the centrifuge chamber to spin-dry the MNA devices to less than 5% moisture content.

h) The dried microneedle array devices can then be separated from the microneedle array production molds for storage under the desired conditions. In some embodiments, CMC90 based devices can be storable between about 50° C. to −86° C.

Examples of fabricated tip-loaded active cargo carrying microneedle arrays can be seen in FIGS. 3A-6B.

Micromilled Master Molds and Spin-Molded Microneedle Arrays

In the following embodiments, micromilling steps are preformed to create microneedle arrays of various specifications. It should be understood, however, that the following embodiments describe certain details of microneedle array fabrication that can be applicable to processes of microneedle array fabrication that do not involve micromilling steps, including the process described above in the previous example.

In the following embodiments, apparatuses and methods are described for fabricating dissolvable microneedle arrays using master molds formed by micromilling techniques. For example, microneedle arrays can be fabricated based on a mastermold (positive) to production mold (negative) to array (positive) methodology. Micromilling technology can be used to generate various micro-scale geometries on virtually any type of material, including metal, polymer, and ceramic parts. Micromilled mastermolds of various shapes and configurations can be effectively used to generate multiple identical female production molds. The female production molds can then be used to microcast various microneedle arrays.

Figure 7:
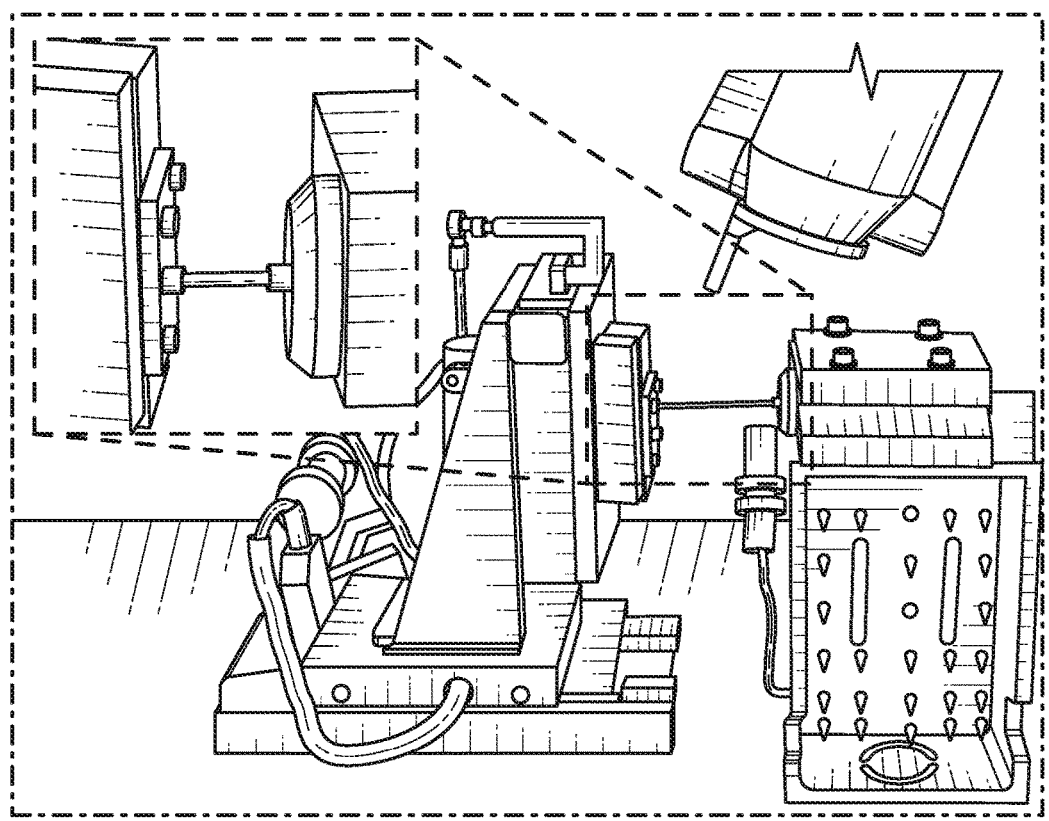
FIG. 7 illustrates a miniature precision-micromilling system used for fabricating microneedle mastermolds.

FIG. 7 illustrates an example of a precision-micromilling system that can be used for fabricating a microneedle mastermold. Mechanical micromilling uses micro-scale (for example, as small as 10 µm) milling tools within precision computer controlled miniature machine-tool platforms. The system can include a microscope to view the surface of the workpiece that is being cut by the micro-tool. The micro-tool can be rotated at ultra-high speeds (200,000 rpm) to cut the workpiece to create the desired shapes. As noted above, the micromilling process can be used to create complex geometric features with many kinds of material. Various types of tooling can be used in the micromilling process, including, for example, carbide micro-tools. In a preferred embodiment, however, diamond tools can be used to fabricate the microneedle arrays on the master mold. Diamond tooling can be preferable over other types of tooling because it is harder than conventional materials, such as carbide, and can provide cleaner cuts on the surface of the workpiece.

Mastermolds can be micromilled from various materials, including, for example, Cirlex® (DuPont, Kapton® polyimide), which is the mastermold material described in the exemplary embodiment. Mastermolds can be used to fabricate flexible production molds from a suitable material, such as SYLGARD® 184 (Dow Corning), which is the production material described in the exemplary embodiment below. The mastermold is desirably formed of a material that is capable of being reused so that a single mastermold can be repeatedly used to fabricate a large number of production molds. Similarly each production mold is desirably able to fabricate multiple microneedle arrays.

Mastermolds can be created relatively quickly using micromilling technology. For example, a mastermold that comprises a 10 mm×10 mm array with 100 microneedles can take less than a couple of hours and, in some embodiments, less than about 30 minutes to micromill Thus, a short ramp-up time enables rapid fabrication of different geometries, which permits the rapid development of microneedle arrays and also facilitates the experimentation and study of various microneedle parameters.

The mastermold material preferably is able to be cleanly separated from the production mold material and preferably is able to withstand any heighted curing temperatures that may be necessary to cure the production mold material. For example, in an illustrated embodiment, the silicone-based compound SYLGARD® 184 (Dow Corning) is the production mold material and that material generally requires a curing temperature of about 80-90 degrees Celsius.

Mastermolds can be created in various sizes. For example, in an exemplary embodiment, a mastermold was created on 1.8 mm thick Cirlex® (DuPont, Kapton® polyimide) and 5.0 mm thick acrylic sheets. Each sheet can be flattened first by micromilling tools, and the location where the microneedles are to be created can be raised from the rest of the surface. Micro-tools can be used in conjunction with a numerically controlled micromilling machine (FIG. 1) to create the microneedle features (e.g., as defined by the mastermold). In that manner, the micromilling process can provide full control of the dimensions, sharpness, and spatial distribution of the microneedles.

Figure 8:
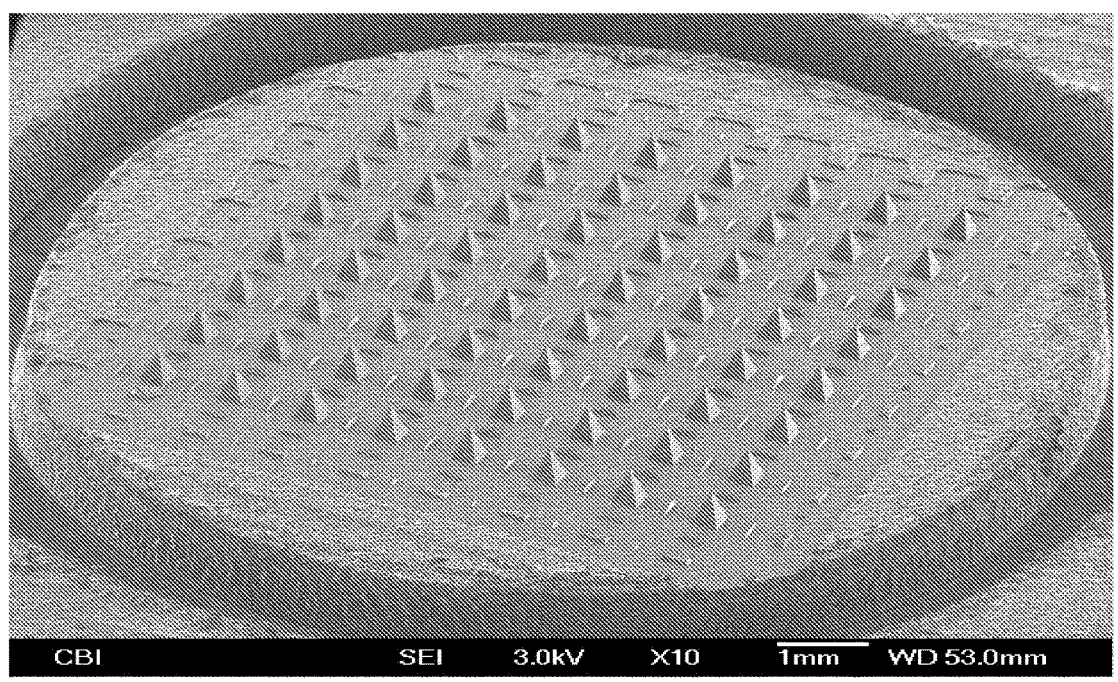
FIG. 8 is an SEM image of a micromilled mastermold with pyramidal needles.

FIG. 8 is an image from a scanning electron microscope (SEM) showing the structure of a micromilled mastermold with a plurality of pyramidal needles. As shown in FIG. 8, a circular groove can be formed around the microneedle array of the mastermold to produce an annular (for example, circular) wall section in the production mold. The circular wall section of the production mold can facilitate the spin-casting processes discussed below. Although the wall sections illustrated in FIG. 9 and the respective mastermold structure shown in FIG. 8 is circular, it should be understood that wall sections or containment means of other geometries can be provided. For example, depending on what shape is desired for the microneedle array device, the containment means can be formed in a variety of shapes including, for example, square, rectangular, trapezoidal, polygonal, or various irregular shapes.

Figure 9:
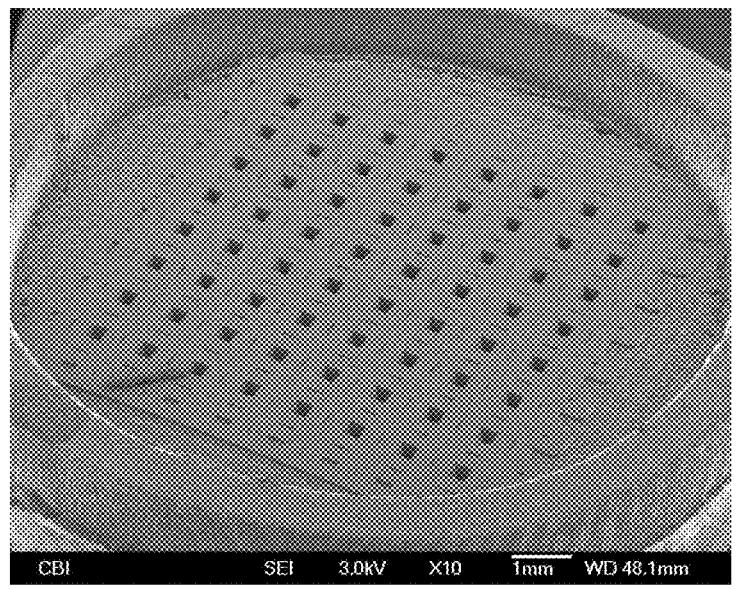
FIG. 9 is an SEM image of a pyramidal production mold.

As discussed above, the production molds can be made from SYLGARD® 184 (Dow Corning), which is a two component clear curable silicone elastomer that can be mixed at a 10:1 SYLGARD® to curing agent ratio. The mixture can be degassed for about 10 minutes and poured over the mastermold to form an approximately 8 mm layer, subsequently degassed again for about 30 minutes and cured at 85° C. for 45 minutes. After cooling down to room temperature, the mastermold can be separated from the cured silicone, and the silicone production mold trimmed to the edge of the circular wall section that surrounds the array (FIG. 9). From a single mastermold, a large number of production molds (e.g., 100 or more) can be produced with very little, if any, apparent deterioration of the Cirlex® or acrylic mastermolds.

Figure 10:
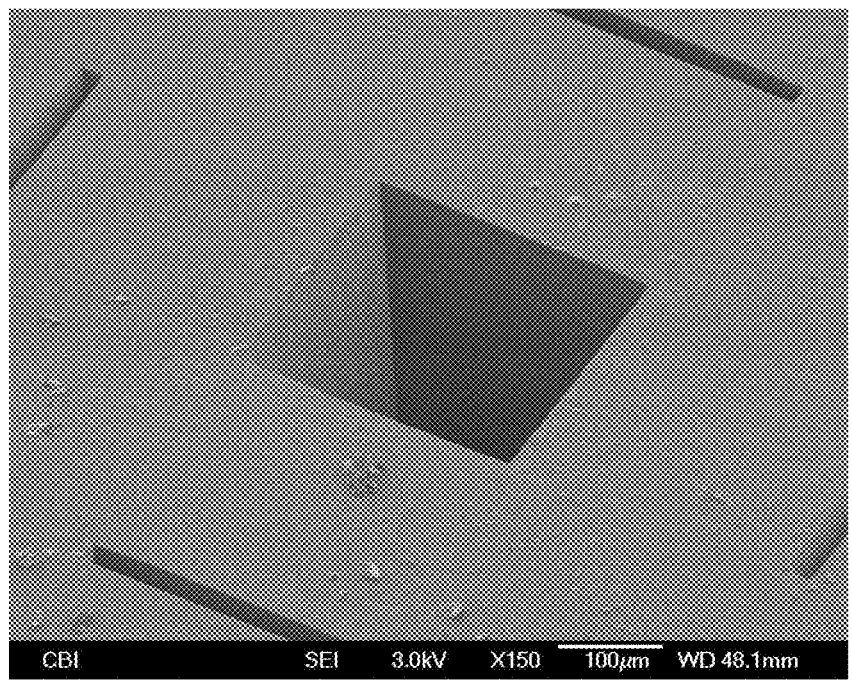
FIG. 10 is an SEM image of an enlarged segment of the production mold, illustrating a pyramidal needle molding well in the center of the image.

FIG. 9 is an SEM image of a pyramidal production mold created as described above. FIG. 10 illustrates an enlarged segment of the production mold with a pyramidal needle molding well in the center of the image. The molding well is configured to receive a base material (and any components added to the base material) to form microneedles with an external shape defined by the molding well.

To construct the microneedle arrays, a base material can be used to form portions of each microneedle that have bioactive components and portions that do not. As discussed above, each microneedle can comprise bioactive components only in the microneedles, or in some embodiments, only in the upper half of the microneedles, or in other embodiments, only in a portion of the microneedle that tapers near the tip. Thus, to control the delivery of the bioactive component(s) and to control the cost of the microneedle arrays, each microneedle preferably has a portion with a bioactive component and a portion without a bioactive component. In the embodiments described herein, the portion without the bioactive component includes the supporting structure of the microneedle array and, in some embodiments, a base portion (e.g., a lower half) of each microneedle in the array.

Various materials can be used as the base material for the microneedle arrays. The structural substrates of biodegradable solid microneedles most commonly include poly(lactic-co-glycolic acid) (PLGA) or carboxymethylcellulose (CMC) based formulations; however, other bases can be used.

CMC is generally preferable to PLGA as the base material of the microneedle arrays described herein. The PLGA based devices can limit drug delivery and vaccine applications due to the relatively high temperature (e.g., 135 degrees Celsius or higher) and vacuum required for fabrication. In contrast, a CMC-based matrix can be formed at room temperature in a simple spin-casting and drying process, making CMC-microneedle arrays more desirable for incorporation of sensitive biologics, peptides, proteins, nucleic acids, and other various bioactive components.

CMC-hydrogel can be prepared from low viscosity sodium salt of CMC with or without active components (as described below) in sterile $dH_2O$. In the exemplary embodiment, CMC can be mixed with sterile distilled water ($dH_2O$) and with the active components to achieve about 25 wt % CMC concentration. The resulting mixture can be stirred to homogeneity and equilibrated at about 4 degrees Celsius for 24 hours. During this period, the CMC and any other components can be hydrated and a hydrogel can be formed. The hydrogel can be degassed in a vacuum for about an hour and centrifuged at about 20,000 g for an hour to remove residual micro-sized air bubbles that might interfere with a spincasting/drying process of the CMC-microneedle arrays. The dry matter content of the hydrogel can be tested by drying a fraction (10 g) of it at 85 degrees Celsius for about 72 hours. The ready-to-use CMC-hydrogel is desirably stored at about 4 degrees Celsius until use.

Active components can be incorporated in a hydrogel of CMC at a relatively high (20-30%) CMC-dry biologics weight ratio before the spin-casting process. Arrays can be spin-cast at room temperature, making the process compatible with the functional stability of a structurally broad range of bioactive components. Since the master and production molds can be reusable for a large number of fabrication cycles, the fabrication costs can be greatly reduced. The resulting dehydrated CMC-microneedle arrays are generally stable at room temperature or slightly lower temperatures (such as about 4 degrees Celsius), and preserve the activity of the incorporated biologics, facilitating easy, low cost storage and distribution.

In an exemplary embodiment, the surface of the production molds can be covered with about 50 µl (for molds with 11 mm diameter) of CMC-hydrogel and spin-casted by centrifugation at 2,500 g for about 5 minutes. After the initial CMC-hydrogel layer, another 50 µl CMC-hydrogel can be layered over the mold and centrifuged for about 4 hours at 2,500 g. At the end of a drying process, the CMC-microneedle arrays can be separated from the molds, trimmed off from excess material at the edges, collected and stored at about 4 degrees Celsius. The production molds can be cleaned and reused for further casting of microneedle arrays.

Figure 11A:
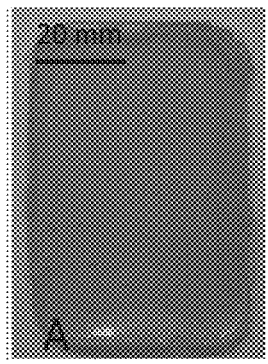
FIGS. 11A-11D illustrate exemplary CMC-solids and embedded active components.
Figure 11B:
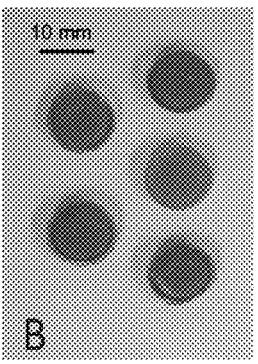
Figure 11C:
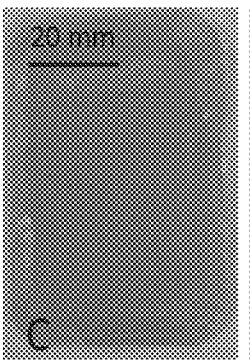
Figure 11D:
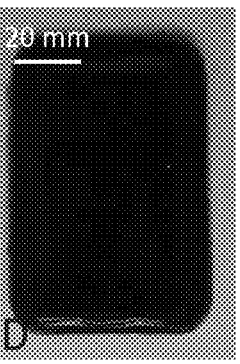

In some embodiments, CMC-solids can be formed with layers that do not contain active components and layers that contain active components. FIGS. 11A-D illustrate CMC-solids with different shapes (FIGS. 11A and 11B) and embedded active cargos on an upper layer which becomes, after micromilling, the portions of the microneedle with the active components. FIG. 11C illustrates micron sized fluorescent particles layered on a surface of a non-active component containing layer and FIG. 11D illustrates toluidine blue examples layered on a surface of a non-active component containing layer.

Figure 12A:
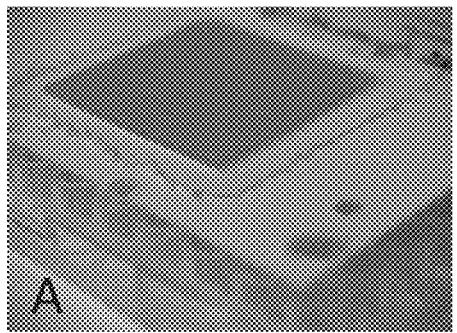
FIGS. 12A-12B illustrate exemplary CMC-solids and embedded active components.
Figure 12B:
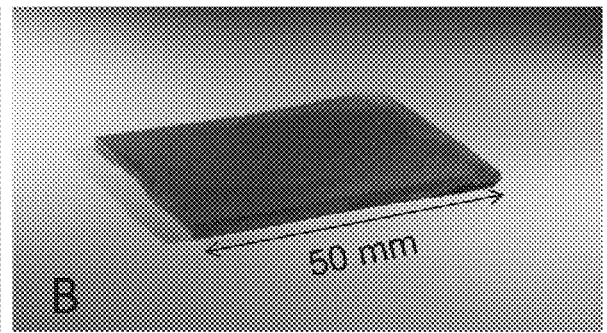

FIGS. 12A and 12B also illustrate CMC-solids with different shapes, with FIG. 12B showing a square shape and FIG. 12B showing a rectangular shape. Both CMC solids can be milled to dimensions for further processing as described herein. It should be understood that the geometries and the active cargo shown herein are not intended to be limited to the exemplary embodiments.

Example 2

CMC-solids can be prepared with defined geometry and active cargo contents in one or more layers of the prepared structure. Examples of active cargos integrated into CMC-solids are described more detail herein. Upon construction of the CMC-solids with embedded active cargo contained in at least one layer of the CMC-solid, the CMC solids can be milled to project-specific dimensions and micro-milled to fabricate microneedle devices as described herein.

Example 3

Figure 13:
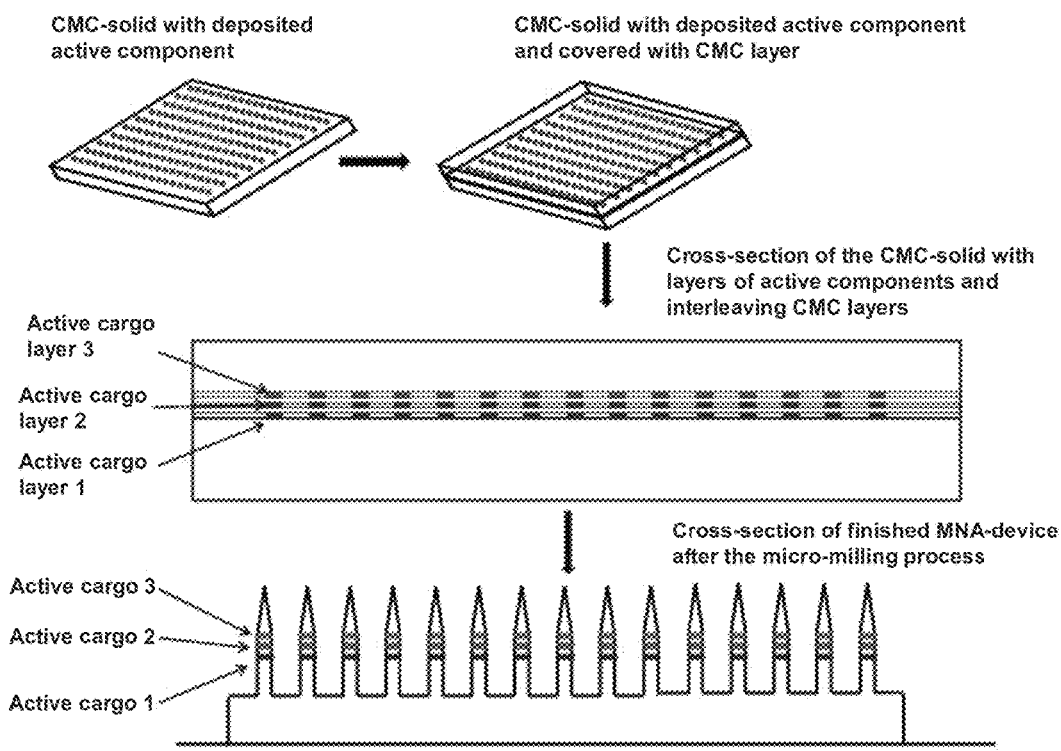
FIG. 13 is a schematic illustration of exemplary vertical multi-layered deposition structures and methods of fabricating the same.

In another embodiment, one or more layers of active cargo can be embedded on CMC-solids for direct micro-milling of the microneedle array. FIG. 13 illustrates a sample representation of vertical multi-layered deposition and CMC embedding of active cargos on CMC-solids for direct micro-milling of MNA devices.

In one exemplary method, microneedle arrays can be fabricated by preparing CMC-solids with a defined geometries and without any active cargo contained therein. Then, blank CMC-solids can be milled to a desired dimension.

As shown in FIG. 13, active cargo(s) can be deposited onto the CMC-solid in project specific geometric patterns for inclusion of the active cargo(s) specifically in the tips of micro-milled MNA devices.

The methods active cargo deposition onto the CMC-solid blank can include, for example:

1) Direct printing with micro-nozzle aided droplet deposition.

2) Transfer from preprinted matrices.

3) Droplet-deposition with computer controlled robotic systems.

Figure 14:
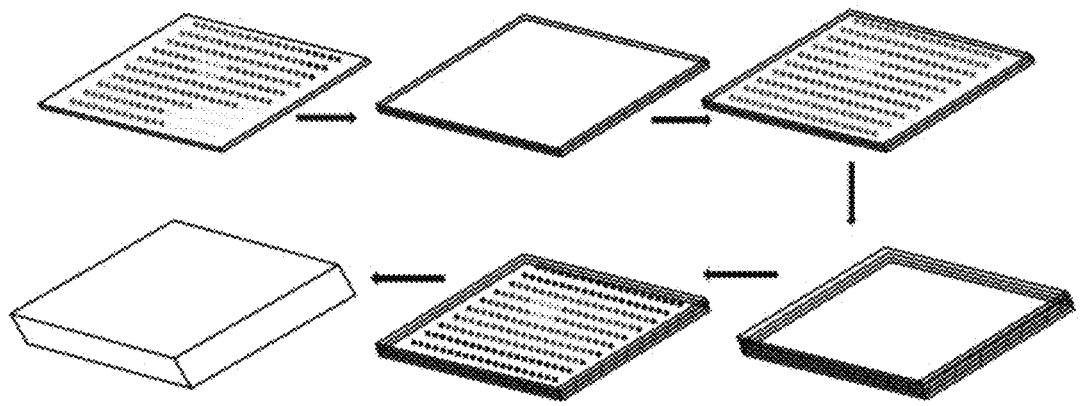
FIG. 14 is a schematic illustration of exemplary microneedle arrays fabricated using layering and spatial distribution techniques of embedded active components.

FIG. 14 illustrates layering and spatial distribution of embedded active cargos in a CMC-solid block. After the first layer is deposited (A) it can be covered with a CMC layer (B) that provides the surface for the subsequent deposition of the active cargo (C). The process can be repeated until all desired layers are deposited and encased in a solid CMC-block suitable for the micro-milling process (D-F).

FIG. 15 illustrates a schematic view of a cross-section of a CMC-block encasing the deposits of the active cargo in a spatially controlled manner (A). The method allows 3-dimensional control and placement of the active components after micro-milling in the MNA-device (B). In panel (B) of FIG. 15, the placement of the active cargos are shown in the stems of the active cargo; however through the control of the milling process the placement can be controlled vertically from the tip to the base of the microneedles. Colors represent different active components or different amount/concentration of the same material.

Thus, a method of vertically layered deposition of active cargos in microneedles is provided by depositing one or more active cargos sequentially on the surface of the CMC-solids in contact with each other or separated by layers of CMC. In some embodiments, horizontal pattern deposition of the active cargos can result in spatial separation of the cargos. By combining vertical and horizontal patterning of active cargo deposition, 3 dimensional delivery and distribution of each of the defined active components can be achieved, further reducing waste of active components during fabrication of microneedle arrays.

Microneedle Integrated Adenovectors

The following embodiments are directed to dissolvable microneedle arrays, such as those described herein, that incorporate infectious viral vectors into the dissolvable matrix of microneedle arrays. Using this technology, for the first time, living viral vectors can be incorporated into microneedle arrays. As described herein, the incorporation of viral vectors within the disclosed microneedle arrays stabilizes the viral vectors so that they maintain their infectivity after incorporation and after prolonged periods of storage. The application of microneedle array incorporated adenovectors (MIAs) to the skin results in transfection of skin cells. In a vaccine setting, we have demonstrated that skin application of MIAs encoding an HIV antigen results in potent HIV specific immune responses. These results are described in detail in the examples below.

Example 4

The microneedle integrated adenovectors preparation method described herein preserves the viability of the adenoviral particles during the preparation and in dry storage. These steps were specifically designed based on the physical and chemical properties of CMC microneedle arrays. Viral viability in CMC microneedle arrays was achieved by Inclusion of low viscosity carboxymethyl cellulose (CMC90) at 2.5% final concentration (step 2.) and by Timed and temperature controlled spin-drying concentration of the adenoviral particles in the tips of the microneedle array devices (step 6).

Controlled partial rehydration of the needle-tip loaded adenoviral particles (step 8.)

Preparation of Tip-loaded Microneedle Integrated Adenovectors (MIAs):

1) Resuspend adenoviral particles at $2 \times 10^9$ particles/ml density in Trehalose-storage buffer (5% trehalose Sigma-Aldrich USA, 20 mM Tris pH7.8, 75 mM NaCl, 2 mM $MgCl_2$, 0.025% Tween 80)

2) Mix resuspended viral stock with equal volume of 5% CMC90 prepared in Trehasole-storage buffer, resulting in a $1 \times 10^9$ particles/ml density adenoviral working stock.

3) Add adenoviral working stock suspension to the surface of microneedle array production molds (as described in detail in other embodiments herein) at 40 µl per cm2 surface area.

4) The molds are centrifuged at 4500 rpm for 10 minutes at 22° C. to fill the needle tips with adenoviral working stock.

5) The excess viral stock is removed and the surface of the molds washed with 100 µl (phosphate buffer saline (PBS) solution per cm2 mold-surface area.

6) The microneedle array-molds containing the adenoviral stock solution only in the needle's cavity are partially spin-dried at 3500 rpm for 10 minutes at 22° C.

7) 100 µl 20% structural, non-cargo containing CMC90 hydrogel in $H_2O$ added to the surface microneedle array-molds' per cm2 mold-area to form the structure of the MIA device.

8) Centrifuge at 4500 rpm for 10 min at 22° C. to fill up the needle cavities with 20% CMC90 and allow 30 min incubation for the rehydration of the adenoviral particles dried in the tips (step 3-6, above).

9) By centrifugation spin-dry the MIA devices to less than 5% moisture content at 3500 rpm for 3 hours at 22° C. with 10 L/min constant air flow through the centrifuge chamber.

10) De-mold the dried MIA devices for storage at 4° C. or −80° C.

Example 5

We have evaluated the potency and stability MNA incorporated recombinant adenoviral particles. Ad5.EGFP was incorporated into CMC hydrogel MNAs to fabricate a final product that contained 1010 virus particles/MNA. Control blank MNAs were prepared identically but without the virus. Batches of Ad5.EGFP and control MNAs were stored at RT, 4° C. and at −86° C. and viral stability was evaluated in infectious assays. Specific transduction activity of the MNA incorporated Ad5.EGFP virus was assessed in vitro using 293T cells. Cells were plated at 2×106/well in six well plates and transduced in duplicate with diluted virus suspension, suspension+empty MNA (control), or Ad5.EGFP MNAs stored at RT, 4° C. and −86° C. for the indicated time periods. As a negative control untransduced wells were included. Initially cell populations were analyzed after 24 h by flow cytometry for GFP expression (representative histogram is shown in FIG. 35).

Figure 35:
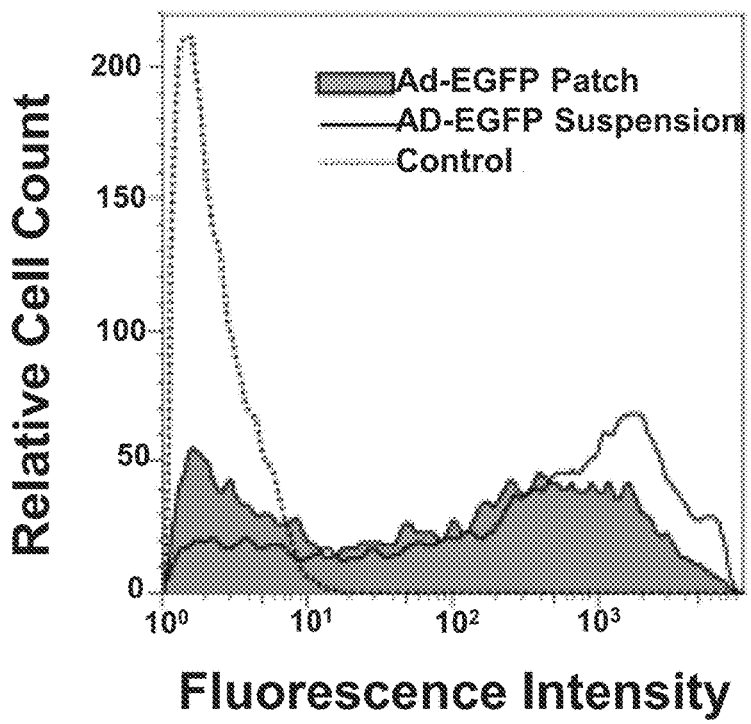
FIG. 35 is a flow cytometry analysis of GFP expressing target 293T cells.
Figure 36:
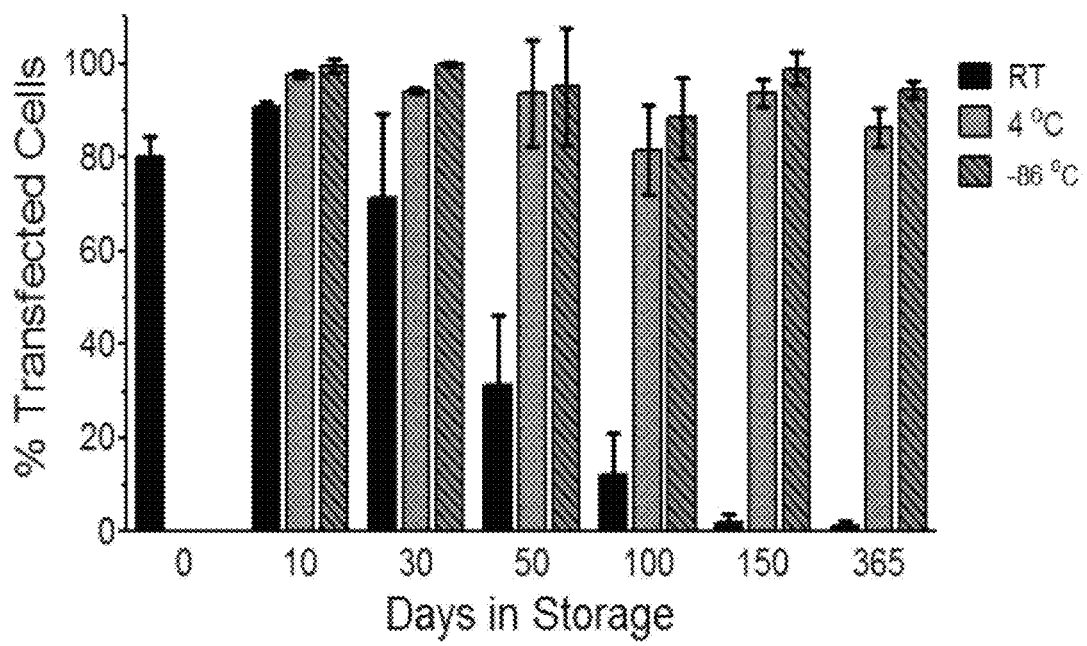
FIG. 36 illustrates the stability of microneedle embedded viruses after a number of days in storage.

As shown in FIG. 35, the incorporation of Ad5.EGFP into MNAs does not reduce transduction efficiency. Flow cytometry analysis of GFP expressing target 293T cells 24 h after transduction with identical titers of Ad5.EGFP either in suspension or incorporated into CMC-patches vs. untransfected control cells. FIG. 36 shows the stability of MNA embedded Ad5.EGFP virus. GFP gene expression was assayed by flow cytometry as in FIG. 37 and normalized to the infection efficiency of −86° C. preserved Ad5.EGFP suspension.

It has been found that the infection efficiency using MNA Ad5.EGFP virus was 87.92±4.5%, which is similar to that observed for traditional −86° C. preserved Ad5.EGFP suspension (FIGS. 35 and 36), suggesting that the manufacturing process does not adversely affect the transduction efficiency of Ad-EGFP viral particles. To asses infectivity over time, the transfection efficiency of freshly prepared −86° C. preserved Ad5.EGFP suspensions was compared to that of MNA incorporated Ad5.EGFP stored for prolonged periods of time at either RT, 4 C, or −86 C. Infectivity (normalized to Ad5.EGFP suspension+empty CMC-patch) is reported for storage periods of up to 365 days (FIG. 36). These results suggest that the infectiousness of MNA Ad5.EGFP is remarkably stable with storage at either 4 C or −86 C, and somewhat stable at RT for up to 30 days.

Figure 37:
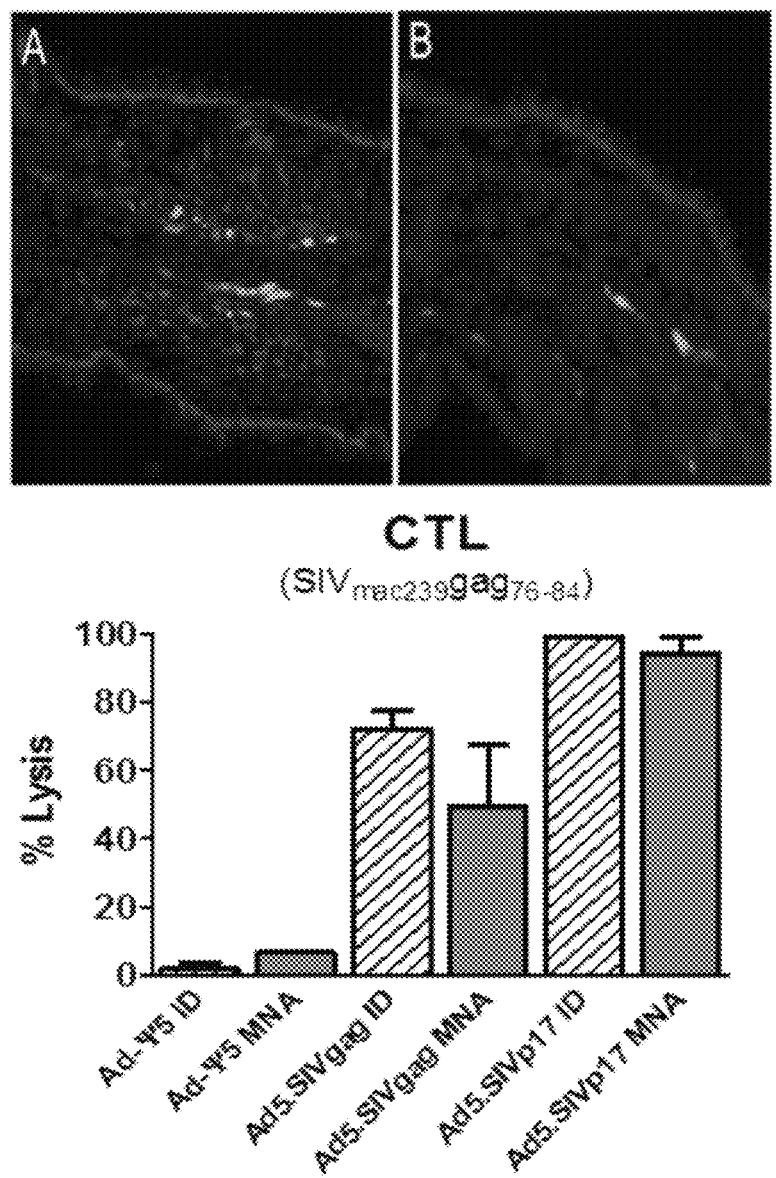
FIG. 37 illustrates the expression and immunogenicity of microneedle array delivered adenovectors.

These results demonstrate that microneedle array delivered Ad transgenes are expressed in the skin and induce potent cellular immune responses. To specifically evaluate gene expression in vivo, we determined GFP expression in skin following either traditional intradermal injection (I.D.) or microneedle array-mediated intracutaneous delivery. We delivered 108 Ad5.GFP viral particles by ID injection or topically via a single microneedle array application (FIG. 37). Skin was harvested 48 h later, cryosectioned, counterstained using blue fluorescent DAPI to identify cell nuclei, and then imaged by fluorescent microscopy. Significant cellular GFP expression was observed following both I.D. and microneedle array delivery. To evaluate immunogenicity, we evaluated antigen-specific lytic activity in vivo following a single I.D. or microneedle array immunization without boosting. For this purpose we immunized groups of mice with E1/E3-deleted Ad5-based vectors that encode codon-optimized SIVmac239 gag full-length or SIVmac239 gag p17 antigens (Ad5.SIV gag, Ad5.SIV gag p17). Empty vector was used as a control (Ad5). We observed potent and similar levels of in vivo lytic activity specific for the dominant SIVgag p17-derived peptide KSLYNTVCV (SIVmac239 gag 76-84) following either I.D. or microneedle array immunization with either Ad5.SIV gag or Ad5.SIV gag p17 (FIG. 37, CTL).

The microneedle array technology disclosed herein can also facilitate clinical gene therapy. It addresses, for example, at least two major limitations of conventional approaches. First, it enables stabilization and storage of recombinant viral vectors for prolonged periods of time. By rendering live virus vectors resistant to high and low temperatures with proven seroequivalence to frozen liquid formulations, microneedle array stabilization will relieve pressures related to the 'cold chain.' Further, integration in microneedle arrays enables precise, consistent and reproducible dosing of viral vectors not achievable by conventional methods. Finally, the viral vector is repackaged in the only necessary delivery device, the biocompatible and completely disposable microneedle array that directs delivery precisely to the superficial layers of the skin. Such a gene delivery platform is useful in providing patient-friendly, clinical gene therapy.

Since these microneedle arrays have been engineered to not penetrate to the depth of vascular or neural structures, gene delivery to human skin will be both painless and bloodless. In addition, the fabrication process is flexible, enabling simple and rapid low cost production with efficient scale-up potential. Also, as a final product, the MIA device it is stable at room temperature and is inexpensive to transport and store. In combination, these structural and manufacturing advantages can enable broad and rapid clinical deployment, making this gene delivery technology readily applicable to the prevention and/or treatment of a broad range of human diseases. Moreover, this approach can be extended to other vector-based vaccine platforms that are currently restricted by the same limitations (e.g., vaccinia virus, AAV etc.). For at least these reasons, the disclosed microneedle arrays and methods of using the same significantly advance the recombinant gene therapy field.

Microneedle Arrays—Exemplary Active Components

Various active components are described in detail below. For convenience, the following examples are based on a microneedle array which is 6.3×6.3 mm. This size, and hence cargo delivery can be varied by increasing or decreasing 2-100 fold.

General considerations for the maximum active cargo quantities include, for example, total needle volume in the array and solubility of the active component(s) in the solvent (generally expected to be <50%).

| Tip Loaded Components: | Amount Tip Loaded into MNA device μg/device (unless indicated differently) | Max. predicted loading capacity |
| --- | --- | --- |

| Live viruses[1] | | |
|---|---|---|
| Ad5.GFP (adeno viral GFP expression vector) | 5 × 10⁸ particles/MNA | 2-5 × 10⁹ particles/MNA |
| Ad-SIVgag (adeno viral gag expression vector) | 5 × 10⁸ particles/MNA | 2-5 × 10⁹ particles/MNA |
| Ad-SIVp17 (adeno viral gag-p17 expression vector) | 5 × 10⁸ particles/MNA | 2-5 × 10⁹ particles/MNA |
| Ψ5 (non-recombinant Ad vector) | 5 × 10⁸ particles/MNA | 2-5 × 10⁹ particles/MNA |
| Lenti-GFP[2] (Lenti viral GFP expression vector) | 5 × 10⁶ particles/MNA | 2-5 × 10⁷ particles/MNA |

Vaccinia virus (immunization)
Recombinant vaccinia virus (gene therapy, genetic engineering)
Seasonal influenza
MMR (Measles, Mumps, Rubella)

| Proteins/Peptides | | |
|---|---|---|
| BSA (FITC labeled) | 240 | 400 |
| OVA (FITC labeled) | 100 | 400 |
| OVA (no label) | 240 | 400 |
| Flu (split vaccine) | 0.22 | (2-5) |

| Epitope Peptides[3] | | |
|---|---|---|
| TRP-2 | 50 | 200 |
| EphA2 (a) | 50 | 400 |
| EphA2 (b) | 50 | 400 |
| DLK-1 | 50 | 200 |
| Multiple epitopes in one MNA | 200 | 400-600 |
| Substance-P (NK-1R ligand) | 15 | |

| Nucleic acids | | |
|---|---|---|
| CpG 1668 | 120 | 250 |
| CpG 2006 | 120 | 250 |
| Poly(I:C) | 250 | 250 |
| Plasmid vectors (High mol. weight DNA) | 100 | 200 |

| Peptides/Nucleic acid combos | |
|---|---|
| OVA/CpG | 250/120 |
| OVA/CpG/poly(I:C) | 250/120/250 |
| Epitope peptides/poly(I:C) | 200/250 |

| Organics | |
|---|---|
| Doxorubicin | 1 to 1000 ug |
| R848 (TLR7/8 ligand) | 6 |
| L733 (NK-1 antagonist) | 2 |
| DNCB (irritant) | 100 |

| Particulates | | |
|---|---|---|
| Micro-particles (1µ diameter microspheres) | 1 × 10⁶ particles/MNA | 2-5 × 10⁷ particles/MNA |

Nano Scale Particles
PLG/PLA Based

| Other Biologic | |
|---|---|
| tumor lysate/CpG | 250/120 |
| tumor lysate/CpG/poly(I:C) | 256/120/250 |
| tumor lysates/poly(I:C) | 200/250 |

Tip-loading of live adenoviruses generally includes the following modifications:
a) The presence of 5% trehalose and 2.5% CMC90 in the tip-loading hydrogel suspension.
b) The temperature of the process is maintained at 22° C. In addition, *Lenti* viral vectors generally require 4° C. processing and vapor trap based humidity controls. Also, short epitope peptides generally are solubilized in DMSO, with the evaporation time of the solvent during tip-loading is 4 hours.

Microneedle Structures and Shapes

For each of the embodiments below, it should be understood that one or more layers of active components can be provided in the microneedles of the microneedle arrays as described above. Thus, for example, in some embodiments, active components are only provided in the area of the microneedle—not in the structural support of the array, such as shown in FIG. 15. Moreover, in other embodiments, the active components are concentrated in the upper half of the microneedles, such as in the tips of the microneedles as shown in FIGS. 3A-4B.

Figures 16A, 16B:
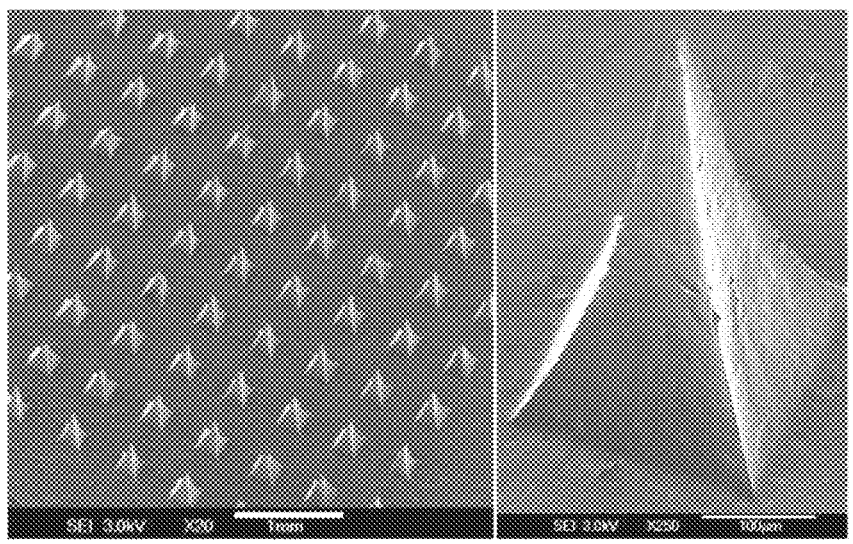
FIG. 16A is an SEM image of a plurality of pyramidal-type molded microneedles.
FIG. 16B is an SEM image of a single pyramidal-type molded microneedle.

FIGS. 16A and 16B are SEM images of a CMC-microneedle array formed with a plurality of pyramidal projections (i.e., microneedles). The average tip diameter of the pyramidal needles shown in FIG. 16A is about 5-10 µm. As shown in FIG. 16B, the sides of the pyramidal needles can be formed with curved and/or arcuate faces that can facilitate insertion in skin.

Figure 17:
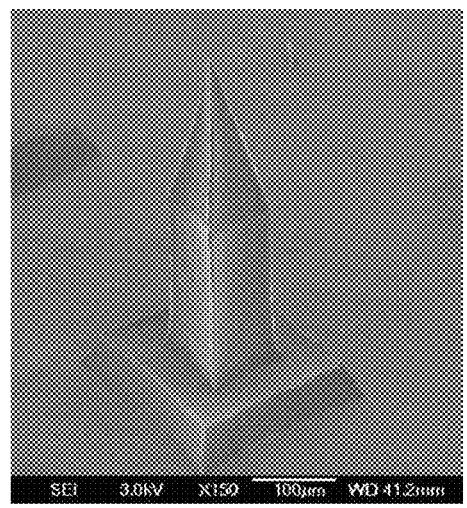
FIG. 17 is an SEM image of a pillar type molded microneedle.

FIG. 17 is another SEM image of a single needle of a microneedle array. The microneedle shown in FIG. 17 is a base-extended pillar type molded CMC-microneedle. The base-extended pillar type microneedle comprises a base portion, which is generally polygonal (for example, rectangular) in cross section, and a projecting portion that extends from the base portion. The projecting portion has a lower portion that is substantially rectangular and tip portion that generally tapers to a point. The tip portion is generally pyramidal in shape, and the exposed faces of the pyramid can be either flat or arcuate. The projecting portion can be half or more the entire length of the needle.

Figure 18:
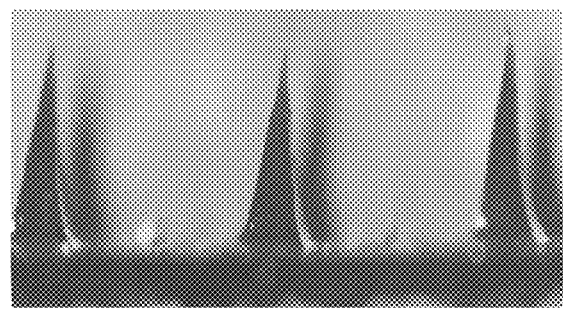
FIG. 18 is a micrograph of pyramidal type molded microneedles.
Figure 19:
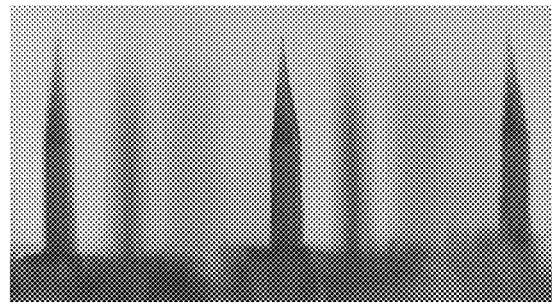
FIG. 19 is a micrograph of pillar type molded microneedles.

FIGS. 18 and 19 illustrate micrographs of pyramidal (FIG. 18) and pillar type (FIG. 19) molded CMC-microneedles. Because the pyramidal needles have a continually increasing cross-sectional profile (dimension) from the needle point to the needle base, as the needle enters the skin, the force required to continue pushing the pyramidal needle into the skin increases. In contrast, pillar type needles have a generally continuous cross-sectional profile (dimension) once the generally rectangular portion of the projection portion is reached. Thus, pillar type needles can be preferable over pyramidal type needles because they can allow for the introduction of the needle into the skin with less force.

Figure 20:
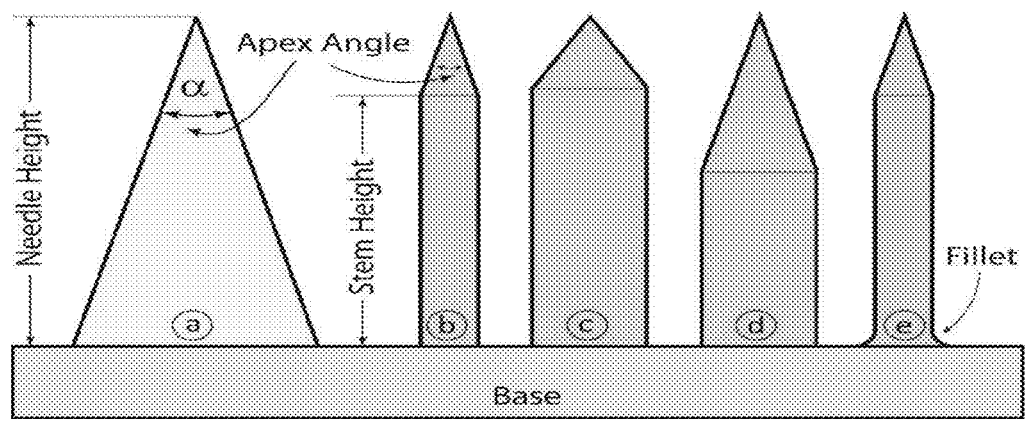
FIG. 20 illustrates various microneedle geometries that can be formed using micromilled mastermolds or by direct micromilling of a block of material.

FIG. 20 illustrates schematic representation of microneedle shapes and structures that are generally suitable for fabrication by spin-casting material into a mastermold formed by micromilling Since the shapes and structures shown in FIG. 20 do not contain any undercuts, they generally will not interfere with the molding/de-molding process. The structures in FIG. 20 include (a) a generally pyramidal microneedle, (b) a "sharp" pillar type microneedle (without the base member of FIG. 8), (c) a "wide" pillar type microneedle, (d) a "short" pillar type microneedle (having a short pillar section and a longer pointed section), and (e) a "filleted" pillar type microneedle.

While the volume of the pyramidal microneedles can be greater than that of the pillar type microneedles, their increasing cross-sectional profile (dimension) requires an increasing insertion force. Accordingly, the geometry of the pyramidal microneedles can result in reduced insertion depths and a reduced effective delivery volume. On the other hand, the smaller cross-sectional area and larger aspect ratio of the pillar microneedles may cause the failure force limit to be lower. The smaller the apex angle $\alpha$, the "sharper" the tip of the microneedle. However, by making the apex angle too small (e.g., below about 30 degrees), the resulting microneedle volume and mechanical strength may be reduced to an undesirable level.

The penetration force of a microneedle is inversely proportional to the microneedle sharpness, which is characterized not only by the included (apex) angle of the microneedles, but also by the radius of the microneedle tip. While the apex angle is prescribed by the mastermold geometry, the tip sharpness also depends on the reliability of the mold. Micromilling of mastermolds as described herein allows for increased accuracy in mold geometry which, in turn, results in an increased accuracy and reliability in the resulting production mold and the microneedle array formed by the production mold.

The increased accuracy of micromilling permits more accurate and detailed elements to be included in the mold design. For example, as discussed in the next section below, the formation of a fillet at the base of a pillar type microneedle can significantly increase the structural integrity of the microneedle, which reduces the likelihood that the microneedle will fail or break when it impacts the skin. While these fillets can significantly increase the strength of the microneedles, they do not interfere with the functional requirements of the microneedles (e.g., penetration depth and biologics volume). Such fillets are very small features that can be difficult to create in a master mold formed by conventional techniques. However, the micromilling techniques described above permit the inclusion of such small features with little or no difficulty.

Mechanical Integrity and Penetration Capabilities

Microneedle arrays are preferably configured to penetrate the stratum corneum to deliver their cargo (e.g., biologics or bioactive components) to the epidermis and/or dermis, while minimizing pain and bleeding by preventing penetration to deeper layers that may contain nerve endings and vessels. To assess the mechanical viability of the fabricated microneedle arrays, tests were performed on the pyramidal and pillar type microneedle arrays as representative variants of array geometry (shown, e.g., in FIGS. 7B and 8). The first set of tests illustrate the failure limit of microneedles, and include pressing the microneedle array against a solid acrylic surface with a constant approach speed, while simultaneously measuring the force and the displacement until failure occurs. The second set of tests illustrate the piercing capability of the microneedles on human skin explants.

Figure 21:
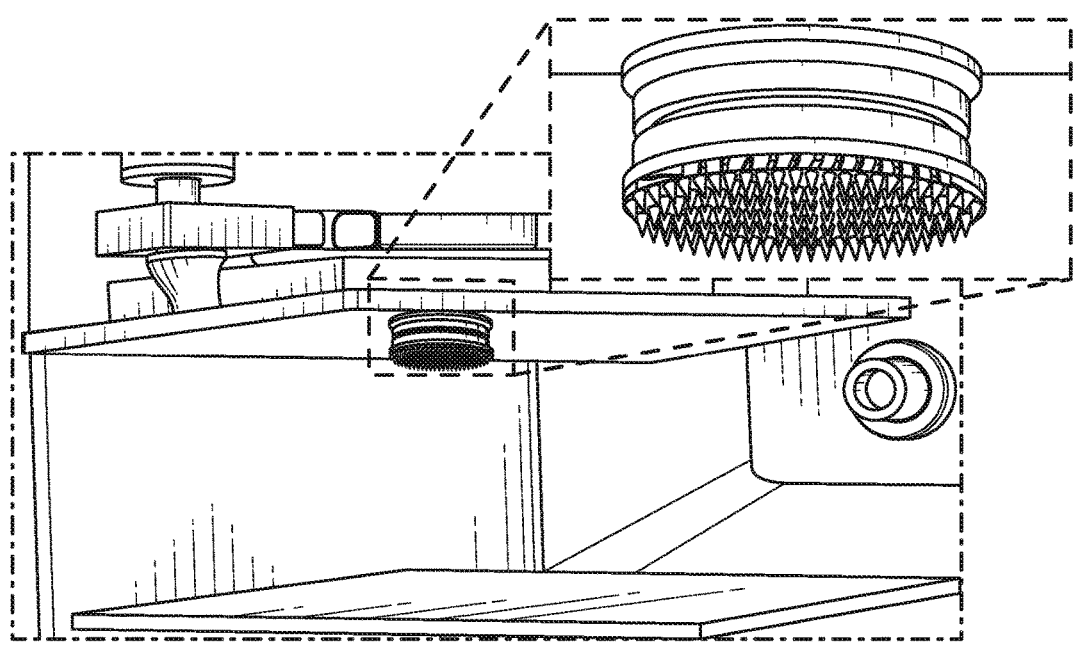
FIG. 21 illustrates a test apparatus for performing failure and piercing tests.

FIG. 21 illustrates a test apparatus designed for functional testing. The sample (i.e., microneedle array) was attached to a fixture, which was advanced toward a stationary acrylic artifact (PMMA surface) at a constant speed of about 10 mm/s speed using a computer-controlled motion stage (ES14283-52 Aerotech, Inc.). A tri-axial dynamometer (9256C1, Kistler, Inc.) that hosted the acrylic artifact enabled high-sensitivity measurement of the forces.

Figure 22:
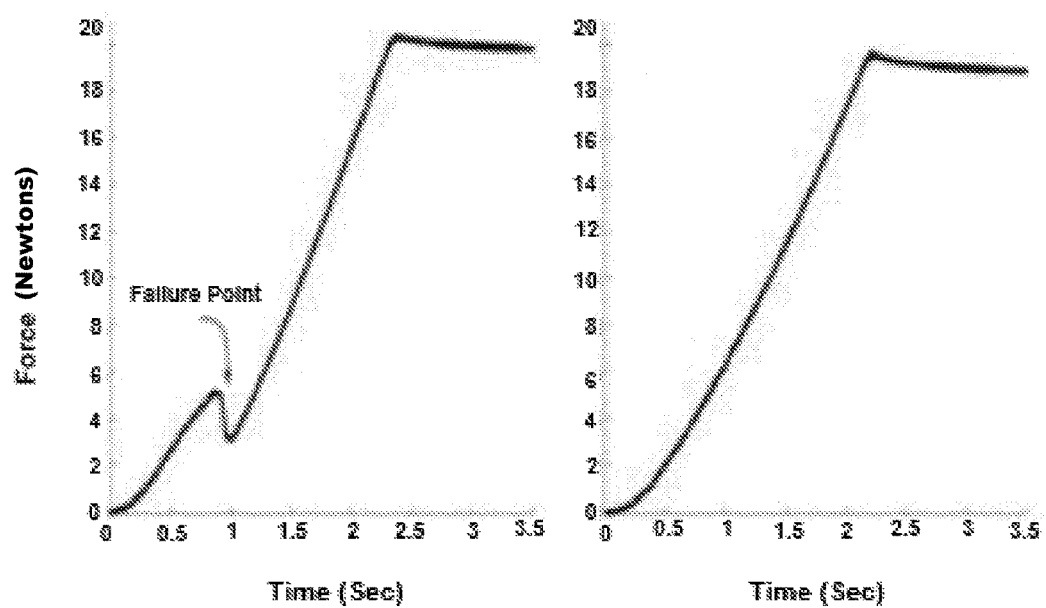
FIG. 22 illustrates force-displacement curves for pillar type microneedles (left) and pyramidal type microneedles (right).
Figure 24A:
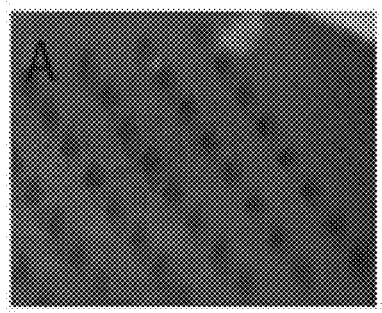
FIGS. 24A-24F show various stereo micrographs of the penetration of pyramidal (A, C, E) and pillar (B, D, F) type microneedles in skin explants.
Figure 24B:
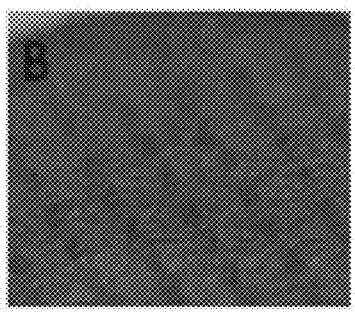
Figure 24C:
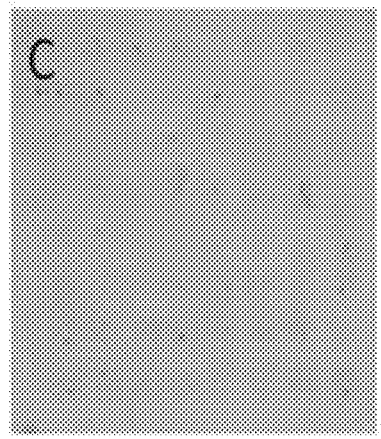
Figure 24D:
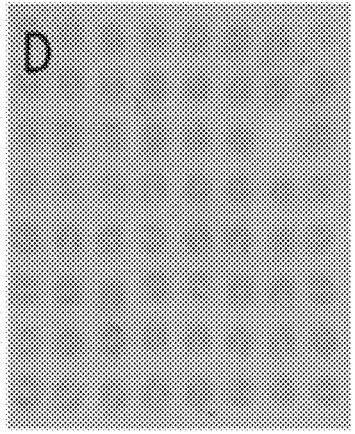
Figure 24E:
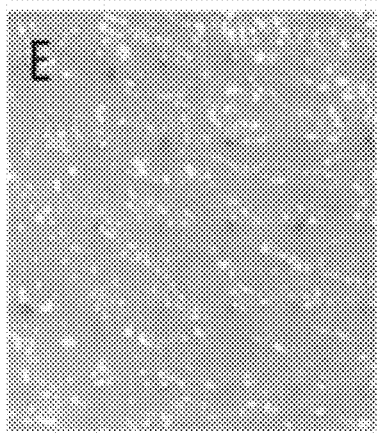
Figure 24F:
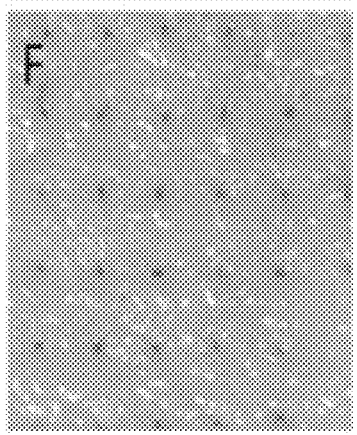

FIG. 22 illustrates force-displacement curves of data measured during failure tests. The curve on the left is representative of data obtained from testing a pillar microneedle sample and the curve on the right is representative of data obtained from testing a pyramid microneedle. As seen in FIG. 22, the failure of these two kinds of microneedles are significantly different; while the pyramidal arrays plastically deform (bend), the pillar type arrays exhibit breakage of the pillars at their base. This different failure behavior lends itself to considerably different displacement-force data. The failure (breakage) event can be easily identified from the displacement-force data as indicated in the figure. Based on the obtained data, the failure point of pillar type microneedles was seen to be 100 mN in average. As only about 40 mN of force is required for penetration through the stratum corneum, the microneedles are strong enough to penetrate human skin without failure. Furthermore, since parallelism between microneedle tips and the acrylic artifact cannot be established perfectly, the actual failure limit will likely be significantly higher than 100 mN (i.e., microneedles broke in a successive manner, rather than simultaneous breakage of most/all microneedles).

The pyramidal microneedles presented a continuously increasing force signature with no clear indication of point of failure. To identify the failure limit for the pyramidal microneedles, interrupted tests were conducted in which the microneedles were advanced into the artifact by a certain amount, and retreated and examined through optical microscope images. This process was continued until failure was observed. For this purpose, the failure was defined as the bending of the pyramidal microneedles beyond 15 degrees.

To further analyze the failure of the microneedles, the finite-elements model (FEM) of the microneedle arrays shown in FIG. 23 was developed. To obtain the mechanical properties (elastic modulus and strength limit) of the CMC material, a series of nanoindentation tests (using a Hysitron nanoindentor). The average elastic modulus and yield strength of the CMC material (as prepared) were 10.8 GPa and 173 MPa, respectively. This indicates that the prepared CMC material has a higher elastic modulus and yield strength than both PMMA (elastic modulus: 3.1 GPa, yield strength: 103 MPa) and polycarbonate (elastic modulus: 2.2 GPa, yield strength: 75 MPa), indicating the superior strength and stiffness of CMC material with respect to other polymers.

Using this data, a series of FEM simulations were conducted. It was predicted from the 1-BM models that failure limit of pyramidal and sharp-pillar (width=134 µm)

microneedles with 600 µm height, 30 degree apex angle, and 20 µm fillet radius were 400 mN (pyramid) and 290 mN (sharp-pillar) for asymmetric loading (5 degrees loading misorientation). Considering that the minimum piercing force requirement is about 40 mN, pyramid and sharp-pillar microneedles would have factors of safety of about 10 and 7.25, respectively.

When the fillet radius is doubled to 40 µm, the failure load for the pillar was increased to 350 mN, and when the fillet radius is reduced to 5 µm, the failure load was reduced to 160 mN, which is close to the experimentally determined failure load. The height and width of the pillars had a significant effect on failure load. For instance, for 100 µm width pillars, increasing the height from 500 µm to 1000 µm reduced the failure load from 230 mN to 150 mN. When the width is reduced to 75 µm, for a 750 µm high pillar, the failure load was seen to be 87 mN.

To evaluate penetration capability, pyramidal and sharp-pillar microneedle arrays were tested for piercing on water-based model elastic substrates and on full thickness human skin. FIG. 24 illustrates stereo micrographs of pyramidal (Panels A, C, and E) and pillar type microneedle arrays (B, D, and F) after 4 minutes of exposure to model elastics. In particular, toluene blue tracer dye was deposited in model elastic substrates (Panels C and D) or freshly excised full thickness human skin explants (Panels E and F) after application of pyramidal or pillar type microneedle arrays.

The model elastic substrate comprised about 10% CMC and about 10% porcine gelatin in PBS gelled at about 4 degrees Celsius for about 24 hours or longer. The surface of the elastics was covered with about 100 µm thick parafilm to prevent the immediate contact of the needle-tips and the patch materials with the water based model elastics. To enable stereo microscopic-imaging, trypan blue tracer dye (Sigma Chem., cat # T6146) was incorporated into the CMC-hydrogel at 0.1% concentration. The patches were applied using a spring-loaded applicator and analyzed after about a 4 minute exposure. Based on physical observation of the dye in the target substrates, the dissolution of the microneedles of the two different geometries was markedly different.

The sharp-pillar needles applied to the model elastic substrate released substantially more tracer dye to the gel matrix than that observed for the pyramidal design (FIG. 24, C vs. D). Images of the recovered patches (FIG. 24, A vs. B) were consistent with this observation, as the degradation of the sharp-pillar needles was more advanced than that of the pyramidal needles. To extrapolate this analysis to a more clinically relevant model, pyramidal and pillar type microneedle arrays were applied to freshly excised full thickness human skin explants using the same force from the spring loaded applicator. Consistent with results from the elastic model, the pyramidal microneedle arrays deposited visibly less tracer dye than the sharp-pillar microneedle arrays (FIG. 24, E vs. F).

To further evaluate penetration and to assess delivery effectiveness to human skin, CMC-microneedle arrays were fabricated with BioMag (Polysciences, Inc., cat#. 84100) beads or fluorescent particulate tracers (Fluoresbrite YG 1 µm, Polysciences Inc., cat#. 15702). The pyramidal CMC-microneedle arrays containing fluorescent or solid particulates were applied to living human skin explants as described previously. Five minutes after the application, surface residues were removed and skin samples were cryo-sectioned and then counterstained with toluene blue for imaging by light microscopy (FIGS. 25A and 25B) or by fluorescent microscopy (FIG. 25C).

Pyramidal CMC-microneedles effectively penetrated the stratum corneum, epidermis, and dermis of living human skin explants, as evidenced by the deposition of Biomag beads lining penetration cavities corresponding to individual needle insertion points (representative sections shown in FIGS. 25A and 25B). In particular, ordered cavities (FIG. 25A, cavities numbered 1-4, toluene blue counterstain, 10×) and deposits of BioMag particles (brown) lining penetration cavities were evident (FIG. 25B, 40×), indicating microneedle penetrated of human skin. Further, analysis of sections from living human explants stained with DAPI to identify cell nuclei and anti-HLA-DR to identify MHC class II+ antigen presenting cells revealed high density fluorescent particulates deposited in the superficial epidermis and dermis, including several particles co-localized with class II+ antigen presenting cells (FIG. 25C, DAPI (blue), HLA-DR+ (red) and fluorescent particles (green), 40×).

These results further demonstrate that the CMC microneedle arrays described herein can effectively penetrate human skin and deliver integral cargo (bioactive components), including insoluble particulates. They are consistent with effective delivery of particulate antigens to antigen presenting cells in human skin, currently a major goal of rational vaccine design.

To further address microneedle array delivery in vivo, the cutaneous delivery of particulate antigen in vivo was modeled by similarly applying fluorescent particle containing arrays to the dorsal aspect of the ears of anesthetized mice. After 5 minutes, patches were removed and mice resumed their normal activity. Three hours or 3 days, ear skin and draining lymph nodes were analyzed for the presence of fluorescent particles. Consistent with observations of human skin, particulates were evident in the skin excised from the array application site (data not shown). Further, at the 3 day time point, substantial numbers of particles were evident in the draining lymph nodes. FIGS. 26A and 26B illustrates substantial numbers of particles that were evident in the draining lymph Nodes (FIG. 26A, 10×), including clusters of particulates closely associated with Class II+ cells (FIG. 26B, 60×) suggesting the presence of lymph node resident antigen presenting cells with internalized particulates.

To quantitatively evaluate the effects of needle geometry on cargo delivery using microneedle arrays, 3H-tracer labeled CMC-microneedle arrays were constructed. The CMC-hydrogel was prepared with 5% wt ovalbumin as a model active component at 25 wt % final dry weight content (5 g/95 g OVA/CMC) and trace labeled with 0.1 wt % trypan blue and 0.5×10$^6$ dpm/mg dry weight 3H-tracer in the form of 3H-thymidine (ICN Inc., cat #2406005). From a single batch of labeled CMC-hydrogel-preparation four batches of 3H-CMC-microneedle arrays were fabricated, containing several individual patches of pyramidal and sharp-pillar needle geometry. The patches were applied to human skin explants as described above and removed after 30 min exposure. The patch-treated area was tape-striped to remove surface debris and cut using a 10 mm biopsy punch. The 3H content of the excised human skin explants-discs was determined by scintillation counting. The specific activity of the 3H-CMC-microneedle patch-material was determined and calculated to be 72,372 cpm/mg dry weight. This specific activity was used to indirectly determine the amount of ovalbumin delivered to and retained in the skin. The resulting data is summarized in Table 1 below.

The tested types of patches were consistent from microneedle array to microneedle array (average standard deviation 24-35%) and batch to batch (average standard deviation 7-19%). The intra-batch variability for both needle geometry was lower than the in-batch value indicating that the insertion process and the characteristics of the target likely plays a primary role in the successful transdermal material delivery and retention. The patch-material retention data clearly demonstrate the foremost importance of the microneedle geometry in transdermal cargo delivery. Pillar-type needle geometry afforded an overall 3.89 fold greater deposition of the 3H labeled needle material than that of the pyramidal needles. On the basis of the deposited radioactive material, it is estimated that the pyramidal needles were inserted about 200 µm deep while the pillar-type were inserted about 400 µm or more.

TABLE 4.2.5.

Transfer of $^3$H-labeled CMC-microneedle material into human skin explants by pyramidal and pillar-type needles.

| Array Batches | Pyramid Needles (cpm/patch) | STDev (%) | Pyramidal Needles OVA Transferred (µg/patch) | Pillar-Type Needles (cpm/patch) | STDev (%) | Pillar-Type Needles OVA Transferred (µg/patch) | Pillar to Pyramid Ratio |
|---|---|---|---|---|---|---|---|
| Batch A | 2459.00 | 17.56 | 1.70 | 11700.50 | 31.52 | 8.08 | 4.76 |
| Batch B | 3273.50 | 57.39 | 2.26 | 12816.50 | 21.45 | 8.85 | 3.92 |
| Batch C | 2757.75 | 46.13 | 1.90 | 12240.00 | 26.77 | 8.46 | 4.44 |
| Batch D | 3782.00 | 36.27 | 2.61 | 10921.50 | 9.32 | 7.55 | 2.89 |
| IntraBatch AVG | 3068.06 | 19.00 | 2.12 | 11919.63 | 6.77 | 8.24 | 3.89 |

Desirably, the microneedle arrays described herein can be used for cutaneous immunization. The development of strategies for effective delivery of antigens and adjuvants is a major goal of vaccine design, and immunization strategies targeting cutaneous dendritic cells have various advantages over traditional vaccines.

The microneedle arrays described herein can also be effective in chemotherapy and immunochemotherapy applications. Effective and specific delivery of chemotherapeutic agents to tumors, including skin tumors is a major goal of modern tumor therapy. However, systemic delivery of chemotherapeutic agents is limited by multiple well-established toxicities. In the case of cutaneous tumors, including skin derived tumors (such as basal cell, squamous cell, Merkel cell, and melanomas) and tumors metastatic to skin (such as breast cancer, melanoma), topical delivery can be effective. Current methods of topical delivery generally require the application of creams or repeated local injections. The effectiveness of these approaches is currently limited by limited penetration of active agents into the skin, non-specificity, and unwanted side effects.

The microneedle arrays of the present disclosure can be used as an alternative to or in addition to traditional topical chemotherapy approaches. The microneedle arrays of the present disclosure can penetrate the outer layers of the skin and effectively deliver the active biologic to living cells in the dermis and epidermis. Delivery of a chemotherapeutic agents results in the apoptosis and death of skin cells.

Further, multiple bioactive agents can be delivered in a single microneedle array (patch). This enables an immuno-chemotherapeutic approach based on the co-delivery of a cytotoxic agent with and immune stimulant (adjuvants). In an immunogenic environment created by the adjuvant, tumor antigens releases from dying tumor cells will be presented to the immune system, inducing a local and systemic anti-tumor immune response capable of rejecting tumor cells at the site of the treatment and throughout the body.

In an exemplary embodiment, the delivery of a biologically active small molecule was studied. In particular, the activity of the chemotherapeutic agent Cytoxan® delivered to the skin with CMC microneedle arrays was studied. The use of Cytoxan® enables direct measurement of biologic activity (Cytoxan® induced apoptosis in the skin) with a representative of a class of agents with potential clinical utility for the localized treatment of a range of cutaneous malignancies.

To directly evaluate the immunogenicity of CMC microneedle array incorporated antigens, the well characterized model antigen ovalbumin was used. Pyramidal arrays were fabricated incorporating either soluble ovalbumin (sOVA), particulate ovalbumin (pOVA), or arrays containing both pOVA along with CpGs. The adjuvant effects of CpGs are well characterized in animal models, and their adjuvanticity in humans is currently being evaluated in clinical trials.

Immunization was achieved by applying antigen containing CMC-microneedle arrays to the ears of anesthetized mice using a spring-loaded applicator as described above, followed by removal of the arrays 5 minutes after application. These pyramidal microneedle arrays contained about 5 wt % OVA in CMC and about 0.075 wt % (20 µM) CpG. As a positive control, gene gun based genetic immunization strategy using plasmid DNA encoding OVA was used. Gene gun immunization is among the most potent and reproducible methods for the induction of CTL mediated immune responses in murine models, suggesting its use as a "gold standard" for comparison in these assays.

Mice were immunized, boosted one week later, and then assayed for OVA-specific CTL activity in vivo. Notably, immunization with arrays containing small quantities of OVA and CpG induced high levels of CTL activity, similar to those observed by gene gun immunization (FIG. 27). Significant OVA-specific CTL activity was elicited even in the absence of adjuvant, both with particulate and soluble array delivered OVA antigen. It is well established that similar responses require substantially higher doses of antigen when delivered by traditional needle injection.

Figure 28:
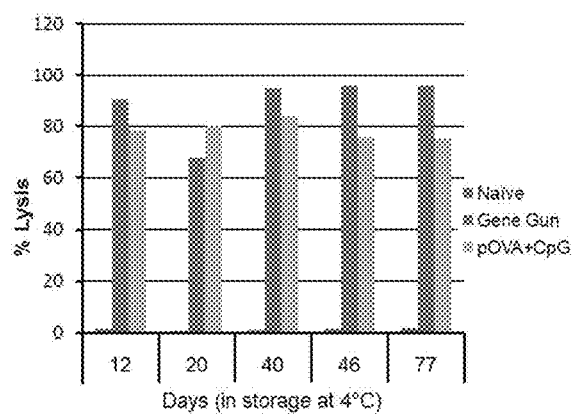
FIG. 28 is a bar graph showing the stability of the active cargo of CMC-microneedle arrays in storage.

To evaluate the stability of fabricated arrays, batches of arrays were fabricated, stored, and then used over an extended period of time. As shown in FIG. 28, no significant deterioration of immunogenicity was observed over storage periods spanning up to 80 days (longest time point evaluated). Thus, the CMC microneedle arrays and this delivery technology can enable effective cutaneous delivery of antigen and adjuvants to elicit antigen specific immunity.

Figures 29A, 29B:
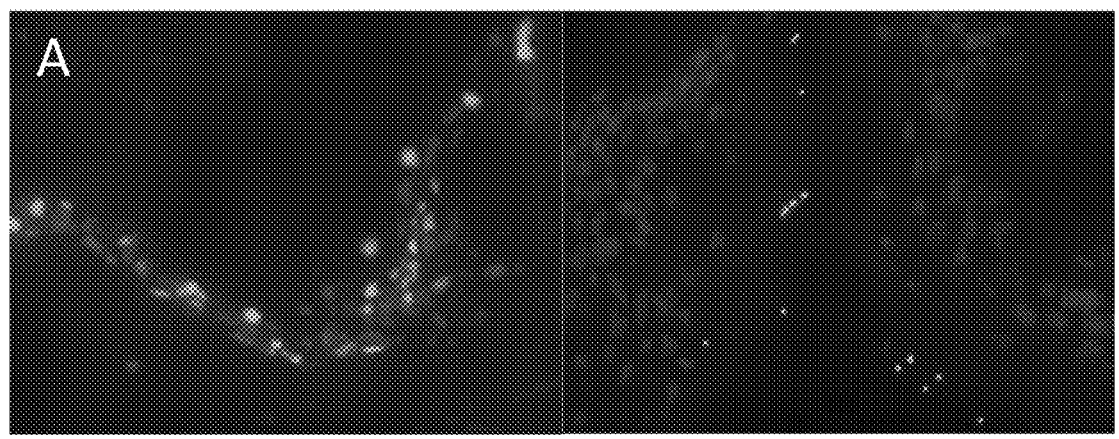
FIGS. 29A and 29B show induction of apoptosis in epidermal cells that have been delivered Cytoxan® (cyclophosphamide) through a microneedle array.

To evaluate the delivery of a biologically active small molecule, pyramidal CMC-microneedle arrays were fabricated with the low molecular weight chemotherapeutic agent Cytoxan® (cyclophosphamide), or with FluoresBrite green fluorescent particles as a control. Cytoxan® was integrated at a concentration of 5 mg/g of CMC, enabling delivery of approximately about 140 µg per array. This is a therapeutically relevant concentration based on the area of skin targeted, yet well below levels associated with systemic toxicities. Living human skin organ cultures were used to assess the cytotoxicty of Cytoxan®. Cytoxan® was delivered by application of arrays to skin explants as we previously described. Arrays and residual material were removed 5 minutes after application, and after 72 hours of exposure, culture living skin explants were cryo-sectioned and fixed. Apoptosis was evaluated using green fluorescent TUNEL assay (In Situ Cell Death Detection Kit, TMR Green, Roche, cat#:11-684-795-910). Fluorescent microscopic image analysis of the human skin sections revealed extensive apoptosis of epidermal cells in Cytoxan® treated skin as shown in FIG. 29A. As shown in FIG. 29B, no visible apoptosis was observed in fluorescent particle treated skin though these particles were evident, validating that the observed area was accurately targeted by the microneedle array.

Direct Fabricated Microneedle Arrays

The micromilling of mastermolds described above allows the production of microneedle arrays with a variety of geometries. In another embodiment, systems and methods are provided for fabricating a microneedle array by directly micromilling various materials, such as dried CMC sheets. The same general tooling that was described above with respect to the micromilling of mastermolds can be used to directly micromilling microneedle arrays.

Direct micromilling of microneedle arrays eliminates the need for molding steps and enables a simplified, scalable, and precisely reproducible production strategy that will be compatible with large scale clinical use. Moreover, direct fabrication of the microneedle arrays through micromilling enables greater control of microneedle geometries. For example, micromilling permits the inclusion of microneedle retaining features such as undercuts and/or bevels, which cannot be achieved using molding processes.

The reproducibility of direct milling of microneedle arrays is particular beneficial. That is, in direct micromilling all of the microneedles are identical as a result of the milling fabrication process. In molding operations, it is not uncommon for some needles to be missing or broken from a given patch as a result of the process of physically separating them from the molds. For use in certain medical applications, the reproducibility of the amount of bioactive components in the array is very important to provide an appropriate level of "quality control" over the process, since irregularities in the needles from patch to patch would likely result in variability in the dose of drug/vaccine delivered. Of course, reproducibility will also be an important benefit to any application that requires FDA approval. Spincast/molded patches would require special processes to assure acceptable uniformity for consistent drug delivery. This quality control would also be likely to result in a certain percentage of the patches "failing" this release test, introducing waste into the production process. Direct micromilling eliminates or at least significantly reduces these potential problems.

Molding processes also have inherent limitations because of the need to be able to fill a well or concavity and remove the cured molded part from that well or concavity. That is because of mold geometries, undercuts must generally be avoided when molding parts or the part will not be removable from the mold. That is, a geometrical limitation of a molded part, such as a molded microneedle array, is that any feature located closer to the apex must be narrower than any feature located toward the base.

Figure 30:
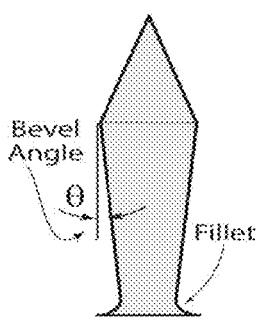
FIG. 30 illustrates a microneedle geometry that can be formed by direct micromilling of a block of material.

Accordingly, in view of these limitations, FIG. 20 illustrates schematic representation of microneedle shapes and structures that are generally suitable for fabrication by molding. That is, the shapes and structures shown in FIG. 20 do not contain any undercuts that would prevent the part (i.e., the microneedles) from being removed from a production mold. In contrast, FIG. 30 illustrates a beveled, undercut microneedle shape that cannot be molded in the manners described herein.

This geometry can only be created through direct fabrication using the proposed micromilling technology. The negative (bevel) angle facilitates better retention of the microneedles in the tissue. In addition, because the microneedle of FIG. 30 has a wider intermediate portion (with a larger cross-sectional dimension) above a lower portion (with a smaller cross-sectional dimension), a greater amount of the bioactive material can be delivered by configuring the microneedle to hold or store the bioactive material in the wider section, which is configured to be retained within the skin. Thus, the larger cross-sectional dimension of the intermediate portion can "carry" the bulk of the bioactive component. Since the lower portion tapers to a narrower cross-sectional dimension, the wider intermediate portion will obtain good penetration for delivery of the bioactive component into the skin layer. A portion above the intermediate portion desirably narrows to a point to facilitate entry of the microneedles into the skin layers.

Another limitation of molded parts is that it can be difficult to precisely fill a very small section of a mold. Since production molds for microneedle arrays comprise numerous very small sections, it can be difficult to accurately fill each well. This can be particularly problematic when the mold must be filled with different materials, such as a material that contains a bioactive component and a material that does not contain a bioactive component. Thus, if the production mold is to be filled with layers, it can be difficult to accurately fill the tiny wells that are associated with each microneedle. Such reproducibility is particularly important, since the microneedles are intended to deliver one or more bioactive components. Thus, even slight variations in the amounts of bioactive component used to fill production molds can be very undesirable.

Also, by using a lamination structure to form a sheet or block that can be micromilled, various active components can be integrated into a single microneedle by vertical layering. For example, in an exemplary embodiment, CMC-hydrogel and CMC-sOVA-hydrogel (80% CMC/20 wt % OVA) were layered into the form of a sheet or block. This composite sheet can be micro-machined using the direct micromilling techniques described herein.

Figure 31:
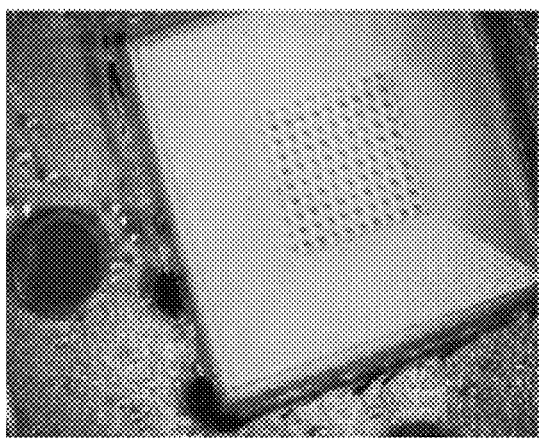
FIG. 31 is a stereo microscopic image of a direct-fabricated solid CMC-microneedle array.
Figure 32:
FIG. 32 is a stereo microscopic image of a portion of the microneedle array of FIG. 31.

FIG. 31 is a stereo-microscopic image analysis of an entire microneedle array. The microneedle comprises a 10×10 array of microneedles. FIG. 32 is an enlarged segment of the microneedle array of FIG. 31. The layering of two components is shown in FIG. 32, which illustrates darker areas of the microneedles at tip portions and lighter areas of the microneedles at base portions. The darker layer at the tip represents the layer comprising a bioactive component, in this case soluble ovalbumin contained in a CMC layer.

Although the formation of a layer containing active material (e.g., antigen) and the subsequent micromilling of the layer (and any other adjacent layers) may require the use of relatively large amounts of the active material, the material can be removed (e.g., in the form of chips), recovered, and recycled. Direct machining technology is not restricted by the geometrical constraints arising from the molding/de-molding approach, and thus, is capable of creating more innovative needle designs (e.g., FIG. 30), which can significantly improve the retained needle-volume and needle retention time in the skin.

The production of sheets or blocks by forming a plurality of layers can provide a solid material that can be micro-machined and which can comprise one or more layers with a bioactive component. For example, a dissoluble solid carboxymethylcellulose polymer based block or sheet with well-defined and controlled dimensions can be fabricated by a lamination process. The resulting sheet or block can be fully machinable, similar to the machining of plastic or metal sheets or blocks. As described herein, the fabrication process can be suitable for the incorporation of bioactive components into the matrix without significantly reducing their activity levels.

As described below, a fabricated sheet of material (such as a CMC based material) can be directly micro-machined/micromilled) to produce one or more microneedle arrays suitable for delivering active ingredients through the skin. This dissoluble biocompatible CMC block-material can be used for the delivery of soluble or insoluble and particulate agents in a time release manner for body surface application. The biocompatible material can be suitable for implants in deeper soft or hard tissue when dissolution of the scaffolding material is required and useful.

The following method can be used to prepare a carboxymethylcellulose (CMC) polymer low viscosity hydrogel to 12.5% concentration. The 12.5% carboxymethylcellulose (CMC) low viscosity hydrogel can be prepared in water or other biocompatible buffer, such as (but not limited to) PBS or HBS. During the preparation of the polymer solution, soluble agents (such as nucleic acid, peptides, proteins, lipids or other organic and inorganic biologically active components) and particulates can be added (e.g. ovalbumin, a soluble agent). Ferrous particulates carrying active ingredients at 20 w/w % of CMC can be used.

The preparation of 1000 g sterile 12.5% CMC hydrogel with no active component can be achieved as follows:

1) Measure 125 g CMC, add 875 g water or other water based solvent.
2) Stir to homogeneity in overhead mixer.
3) Autoclave homogenate to sterility at 121 degrees Celsius for 1 hour (the autoclaving step can reduce viscosity for improved layering)
4) Cool to 22 degrees Celsius.
5) Vacuum treat the resulting material at 10 torr and 22 degrees Celsius for 1 hour to remove trapped micro-bubbles.
6) Centrifuge product at 25,000 g for 1 hour in vacuum chambered centrifuge (for floating and further removing residual micro bubbles).
7) Store the CMC-hydrogel product at 4 degrees Celsius.

The preparation of 1000 g sterile 12.5 w/w % dry content 20/80% ovalbumin/CMC hydrogel can be achieved as follows:

1) Measure 100 g CMC add 650 g water or other water based solvent.
2) Stir to homogeneity in overhead mixer.
3) Autoclave homogenate to sterility at 121 degrees Celsius for 1 hour (this autoclaving step can reduce viscosity for improved layering).
4) Cool to 22 degrees Celsius.
5a) Dissolve 25 g ovalbumin in 225 g water.
5b) Sterile filter ovalbumin solution on 0.22 μm pore sized filter.
6) Mix to homogeneity, under sterile conditions the 750 g CMC hydrogel with 250 g sterile ovalbumin solution.
7) Vacuum treat the resulting material at 10 torr and 22 degrees Celsius for 1 hour to remove trapped micro-bubbles.
8) Centrifuge product at 25,000 g for 1 hour in vacuum chambered centrifuge (for floating and further removing residual micro bubbles).
9) Store the CMC-hydrogel product at 4 degrees Celsius.

The preparation of 100 g sterile 12.5 w/w % dry content 20/80% particulate-ovalbumin/CMC hydrogel can be achieved as follows:

1) Measure 10 g CMC add 87.5 g water or other water based solvent.
2) Stir to homogeneity in overhead mixer.
3) Autoclave homogenate to sterility at 121 degrees Celsius for 1 hour (this autoclaving step can reduce viscosity for improved layering).
4) Cool to 22 degrees Celsius.
5) Disperse 2.5 g particulate-ovalbumin in the 97.5 g, 22 degrees Celsius CMC-hydrogel and mix to homogeneity, under sterile conditions.
6) Vacuum treat the resulting material at 10 torr and 22 degrees Celsius for 2 hour to remove trapped micro-bubbles.
7) Centrifuge product at 3,000 g for 1 hour in vacuum chambered centrifuge (for floating and further removing residual micro bubbles).
8) Store the CMC-hydrogel product at 4 degrees Celsius.

Note in this example, particulate-ovalbumin is prepared from activated iron beads reaction to ovalbumin. However, it should be noted that the above descriptions are only exemplary embodiments and other compounds and active ingredients can be used.

A solid block/sheet carboxymethylcellulose (CMC) can be fabricated in the following manner using the low viscosity CMC-hydrogels described above.

The fabrication process can comprise a laminar spreading of the polymer at a defined thickness and a drying of the layered polymer to less than about 5% water content using sterile dried air flow over the surface of the polymer layer. The above two acts can repeated until the desired block thickness is achieved.

Figure 33:
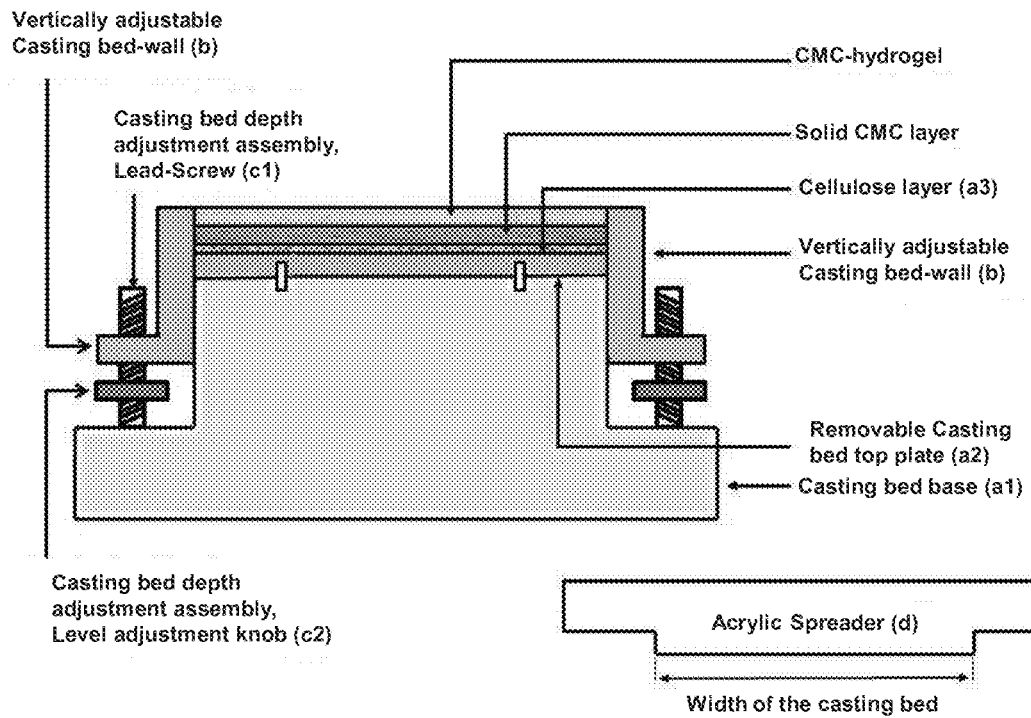
FIG. 33 is a schematic cross-sectional view of a casting-mold assembly for creating a block or sheet of material for direct micromilling.

A method of performing a laminar CMC-hydrogel layering of a defined thickness over the casting mold assembly is described with reference to FIG. 33. FIG. 33 illustrates a cross-sectional view of the casting-mold assembly which includes: (a) casting bed; (b) adjustable casting bed wall; (c) casting-bed depth adjustment assembly; and (d) an acrylic spreader. It should be noted that FIG. 33 is not drawn to scale or otherwise shown with elements in their proper proportions.

The casting mold assembly can be constructed from acrylic (Plexiglas) and can comprise a casting bed base unit, a vertically adjustable hydrophobic casting-bed wall, and a casting-bed adjustment mechanism. The casting bed base unit (a1) can include a removable/replaceable casting bed top plate (a2) with an attached cellulose layer (a3). The cellulose layer can be about 0.5 mm in thickness. The vertically adjustable hydrophobic casting-bed wall (b) can be adjusted using the casting-bed depth adjustment mechanism, which can be comprised of lead-screw (c1) and level adjustment knob (c2). In the illustrated embodiment, a quarter turn of this knob can result in a 0.5 mm lift of the bed wall.

Initially, the adjustable casting bed wall can be set to height where the distance between the acrylic spreader and the cellulose layer of the bed is about 1 mm when the spreader is in position. A predefined volume (e.g., about 0.1 ml/cm2) of the 12.5% CMC-hydrogel can be added and layered. The layer can be evened or leveled by sliding the acrylic spreader (d) on the top surface of the adjustable casting wall to yield an even layer of about 1 mm of CMC-hydrogel. The layered CMC-hydrogel can be dried to a solid phase in the drying apparatus shown in FIG. 34 and described in more detail below.

The layering and drying steps can be repeated until the desired layered structure (sheet) is achieved. The casting bed wall can be raised by an appropriate amount during the addition of each layer. For example, after adding each layer, the bed wall can be raised or lifted by about 0.5 mm Thus, the above-described cycle can deposit about 0.5 mm solid CMC layer. The process (e.g., the layering of material, the raising of bed wall, etc.) can be repeated until the desired block thickness achieved.

Figure 34:
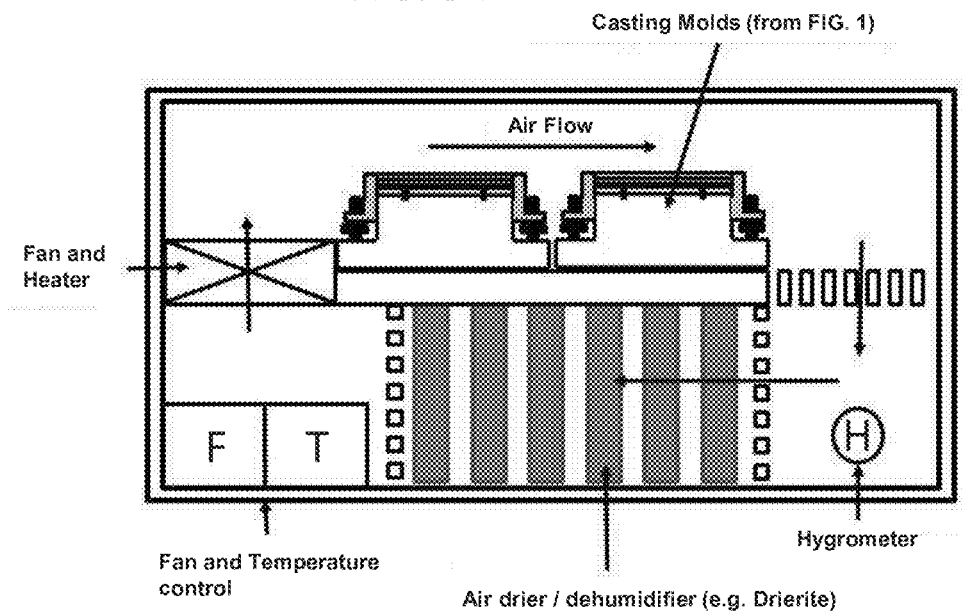
FIG. 34 is a schematic cross-sectional view of a drying apparatus that can be used to dry a block or sheet of material for direct micromilling.

The layered CMC-hydrogel polymer can be dried in various manners. For example, FIG. 34 illustrates a drying apparatus that can be used to dry the various deposited layers of the sheet material. It should be noted that FIG. 34 is not drawn to scale or otherwise shown with elements in their proper proportions. A fan can provide continuous gas flow (e.g., air or other inert gas, such as nitrogen) over the CMC-hydrogel layered in the casting mold assembly. The gas flow will result in a gentle dehydration of the CMC-hydrogel layer. The drying speed can be adjusted to prevent or reduce gas enclosures (e.g., air bubbles) in the solid CMC product. The humid air over the layer can be dried over desiccant (e.g., an air dryer or dehumidifier), temperature adjusted, and returned over the hydrogel again by the speed-controlled fan. A hygrometer can be positioned on the humid side of the chamber to provide an indication of the status of the drying process. After a predetermined dryness has been achieved, as indicated by the hygrometer, the drying process can be ended.

Airflow can be adjusted to affect the drying speed. In the exemplary embodiment, the airflow is controlled to be between about 0.1-2.0 m/sec; the temperature is between ambient and about 50 degrees Celsius. Using these configurations, the drying time of a single layer CMC-hydrogel can be about 0.5-4 hours depend on the airflow and the set temperature.

The pure CMC based product can be transparent, light off white, or amber colored. Its specific gravity can be about 1.55-1.58 g/ml. The product is desirably free of microbubbles and otherwise suitable for fabricating micron scale objects. The physical characterization of the final block/sheet product (hardness, tensile strength, etc.) can vary, but should generally be able to resist physical stresses associated with micromilling.

As described above, the microneedle arrays disclosed herein are capable of providing reliable and accurate delivery methods for various bioactive components. The structural, manufacturing, and distribution advantages characteristic of the above-described microneedle arrays can be particularly applicable for use in delivering vaccines. Advantages of these microneedle arrays include (1) safety, obviating the use of needles or living vectors for vaccine delivery, (2) economy, due to inexpensive production, product stability, and ease of distribution, and 3) diversity, via a delivery platform compatible with diverse antigen and adjuvant formulations.

Moreover, cutaneous immunization by microneedle array has important advantages in immunogenicity. The skin is rich in readily accessible dendritic cells (DCs), and has long been regarded as a highly immunogenic target for vaccine delivery. These dendritic cell populations constitute the most powerful antigen presenting cells (APCs) identified thus far. For example, genetic immunization of skin results in transfection and activation of dendritic cells in murine and human skin, and these transfected dendritic cells synthesize transgenic antigens, migrate to skin draining lymph nodes, and efficiently present them through the MHC class I restricted pathway to stimulate CD8+ T-cells. The immune responses induced by skin derived DCs are remarkably potent and long-lasting compared to those induced by other immunization approaches. Recent clinical studies demonstrate that even conventional vaccines are significantly more potent when delivered intradermally, rather than by standard intramuscular needle injection. Thus, microneedle arrays can efficiently and simultaneously deliver both antigens and adjuvants, enabling both the targeting of DCs and adjuvant engineering of the immune response using the same delivery platform.

Cancer Therapy Applications

Bioactive components used with the microneedle arrays described herein can include one or more chemotherapeutic agents. Effective and specific delivery of chemotherapeutic agents to tumors, including skin tumors is a major goal of modern tumor therapy. However, systemic delivery of chemotherapeutic agents is limited by multiple well-established toxicities. In the case of cutaneous tumors, including skin derived tumors (such as basal cell, squamous cell, Merkel cell, and melanomas) and tumors metastatic to skin (such as breast cancer, melanoma), topical delivery can be effective. Current methods of topical delivery generally require the application of creams or repeated local injections. The effectiveness of these approaches is currently limited by limited penetration of active agents into the skin, non-specificity, and unwanted side effects.

The microneedle arrays of the present disclosure can be used as an alternative to or in addition to traditional topical chemotherapy approaches. The microneedle arrays of the present disclosure can penetrate the outer layers of the skin and effectively deliver the active biologic to living cells in the dermis and epidermis. Delivery of a chemotherapeutic agents results in the apoptosis and death of skin cells.

Further, multiple bioactive agents can be delivered in a single microneedle array (patch). This enables an immuno-chemotherapeutic approach based on the co-delivery of a cytotoxic agent with and immune stimulant (adjuvants). In an immunogenic environment created by the adjuvant, tumor antigens releases from dying tumor cells will be presented to the immune system, inducing a local and systemic anti-tumor immune response capable of rejecting tumor cells at the site of the treatment and throughout the body.

Example 6

In an exemplary embodiment, the delivery of a biologically active small molecule was studied. In particular, the activity of the chemotherapeutic agent Cytoxan® delivered to the skin with CMC microneedle arrays was studied. The use of Cytoxan® enables direct measurement of biologic activity (Cytoxan® induced apoptosis in the skin) with a representative of a class of agents with potential clinical utility for the localized treatment of a range of cutaneous malignancies.

To directly evaluate the immunogenicity of CMC microneedle array incorporated antigens, the well characterized model antigen ovalbumin was used. Pyramidal arrays were fabricated incorporating either soluble ovalbumin (sOVA), particulate ovalbumin (pOVA), or arrays containing both pOVA along with CpGs. The adjuvant effects of CpGs are well characterized in animal models, and their adjuvanticity in humans is currently being evaluated in clinical trials.

Immunization was achieved by applying antigen containing CMC-microneedle arrays to the ears of anesthetized mice using a spring-loaded applicator as described above, followed by removal of the arrays 5 minutes after application. These pyramidal microneedle arrays contained about 5 wt % OVA in CMC and about 0.075 wt % (20 µM) CpG. As a positive control, gene gun based genetic immunization strategy using plasmid DNA encoding OVA was used. Gene gun immunization is among the most potent and reproducible methods for the induction of CTL mediated immune responses in murine models, suggesting its use as a "gold standard" for comparison in these assays.

Mice were immunized, boosted one week later, and then assayed for OVA-specific CTL activity in vivo. Notably, immunization with arrays containing small quantities of OVA and CpG induced high levels of CTL activity, similar to those observed by gene gun immunization. Significant OVA-specific CTL activity was elicited even in the absence of adjuvant, both with particulate and soluble array delivered OVA antigen. It is well established that similar responses require substantially higher doses of antigen when delivered by traditional needle injection.

To evaluate the stability of fabricated arrays, batches of arrays were fabricated, stored, and then used over an extended period of time. No significant deterioration of immunogenicity was observed over storage periods spanning up to 80 days (longest time point evaluated). Thus, the CMC microneedle arrays and this delivery technology can enable effective cutaneous delivery of antigen and adjuvants to elicit antigen specific immunity.

To evaluate the delivery of a biologically active small molecule, pyramidal CMC-microneedle arrays were fabricated with the low molecular weight chemotherapeutic agent Cytoxan® (cyclophosphamide), or with FluoresBrite green fluorescent particles as a control. Cytoxan® was integrated at a concentration of 5 mg/g of CMC, enabling delivery of approximately about 140 µg per array. This is a therapeutically relevant concentration based on the area of skin targeted, yet well below levels associated with systemic toxicities. Living human skin organ cultures were used to assess the cytotoxicty of Cytoxan®. Cytoxan® was delivered by application of arrays to skin explants as we previously described. Arrays and residual material were removed 5 minutes after application, and after 72 hours of exposure, culture living skin explants were cryo-sectioned and fixed. Apoptosis was evaluated using green fluorescent TUNEL assay (In Situ Cell Death Detection Kit, TMR Green, Roche, cat#:11-684-795-910). Fluorescent microscopic image analysis of the human skin sections revealed extensive apoptosis of epidermal cells in Cytoxan® treated skin. No visible apoptosis was observed in fluorescent particle treated skin though these particles were evident, validating that the observed area was accurately targeted by the microneedle array.

Example 7

In another embodiment, topical treatment of established tumors with doxorubicin and/or Poly(I:C) integrated into MNAs established tumor regression and durable immunity that can protect from subsequent lethal systemic tumor challenges.

Novel therapeutic approaches for treating established skin tumors were provided based on the combined effect of MNA delivered chemotherapy, MNA delivered immunostimulant therapy, and/or MNAs delivering combination chemo-immunotherapy. The B16 melanoma model was used as a model tumor to test these novel approaches. The B16 melanoma model is very well studied, and is one of the most aggressive murine skin cancers. Of all skin tumor models available, an established B16 tumor is among the most difficult to treat. Further, B16 has a very high metastatic potential, enabling a clinically relevant assessment of systemic tumor immunity.

B16 skin tumors were established in normal mice by injection. Visible established cutaneous tumors were treated once weekly for three weeks with MNAs containing either doxorubicin alone, Poly(I:C) alone, or doxorubicin and Poly(I:C) incorporated into the same MNA. The doxorubicin dose chosen corresponds to an MNA dose that induces apoptosis in human skin without causing necrosis. Tumor growth and survival were measured regularly for the duration of the study. Treatment with MNAs containing doxorubicin alone slowed tumor growth, and improved survival (30%) compared to that observed in untreated tumor bearing animals that had a 100% mortality rate. Further, treatment with MNAs containing Poly(I:C) alone slowed tumor growth, and improved survival (50%) compared to that observed in untreated tumor bearing animals that had a 100% mortality rate. Remarkably, treatment with containing both doxorubicin+Poly(I:C) substantially slowed tumor growth in all animals, and eradicated tumors completely in 8 out of 10 mice. This was reflected in 80% long term survival extending through day 70.

Surviving animals were evaluated to determine whether they developed long-term immunity against these same tumors. Specifically, systemic immunity was evaluated in these animals, including the durability of the immune response and the capacity of surviving animals to survive IV challenge. In particular, sixty days after the initial MNA treatment, mice were treated with a lethal dose of B16. Fourteen days later, mice were sacrificed and lung metastases were quantified microscopically. Treated mice demonstrated dramatically reduced numbers of lung lesions compared to naïve controls. Taken together, these results demonstrate the capacity of MNAs to deliver chemotherapeutic agents, immune stimulants, and combinations of these agents to both induce regression of established skin tumors, and to simultaneously induce durable systemic tumor specific immune responses capable of protecting the subject from subsequent tumors.

In another embodiment, Poly-ICLC can be substituted for Poly(I:C), and MNAs can be formed, for example, with Poly-ICLC in combination with at least one other chemotherapeutic agent (e.g., doxorubicin).

As discussed above, the one or more chemotherapeutic agents can include one or more immunostimulants agents (specific and non-specific) known by those skilled in the art to stimulate the immune system to reject and destroy tumors, such as Poly(I:C) and Poly-ICLC. These immunostimulants can be integrated into the MNAs along with other chemotherapeutic agents, such as cytotoxic agents like doxorubicin Immunostimulants that can be used in the manner described herein include adjuvants, toll-like receptors (TLRs), ribonucleotides and deoxyribonucleotides, double stranded RNAs (dsRNA), and derivatives of Poly(I:C).

Compositions Comprising Bioactive Components and Methods of Forming the Same

As discussed in detail above, dissolvable microneedle arrays can be used for transdermal delivery of drugs and biologics to human skin. Such microneedle arrays can include one or more bioactive components, including drugs, adjuvants, antigens, and chemotherapeutic agents such as Doxorubicin.

In some embodiments, one or more bioactive molecules can be linked to carboxymethylcellulose or similar biocompatible components. The methodology for chemically combining these agents can include methods that create a linkage designed to release one or more active components in target microenvironments by utilizing unique features of the microenvironment. This can include, for example, the acidic environment of a cellular compartment or vesicle, or the reducing environment of a tumor. In another embodiment of this invention this can include the combined delivery of carboxymethylcellulose conjugate and an agent facilitating cleavage of the conjugate that releases an active component. Delivery of the release facilitating agent can be simultaneous or sequential with delivery of the conjugate.

Advantages of providing cleavable bioactive components include the capability to deliver bioactive components in a protected fashion, limiting drug release to the target site thereby enhancing effective delivery concentrations while minimizing systemic or non-specific exposures. Further, in the event that the bioactive component is a targeting entity, drug release can be targeted to specific cell types or cells with certain metabolic features. A further advantage is the potential for protracted or sustained release delivery.

Carboxymethylcellulose or similar biocompatible components can be selected to enable fabrication into dissolvable microneedle arrays such as the arrays and methods of fabrication described herein. Alternatively, these conjugates can be delivered into the body by other means such as needle injection or ingestion.

As described herein, molecules of bioactive components, such as pharmaceutically active compounds, can be chemically conjugated to carboxymethylcellulose. In some embodiments, this is achieved using a cleavable bond capable of releasing the active chemical moiety in certain biologically natural or engineered environments. This technology can be useful for controlled and targeted drug delivery. Further, due to structural features of CMC, CMC-drug conjugates can be delivered by traditional methods including needle injection, and by novel delivery strategies by physically hardening the conjugate into solid structures that can be implanted, or that can serve as a combination drug/delivery device in the same entity. Examples of the latter would include CMC-drug conjugates fabricated into dissolvable microneedle arrays.

The example presented below includes a chemotherapeutic agent, Doxorubicin, which can be chemically linked to carboxymethylcellulose through a cleavable disulfide bond. However, a cleavable disulfide bond is just one chemical linkage strategy that can be used to link molecules of a bioactive component to a substrate, such as a CMC substrate. For example, in addition to disulfide bonds, other chemical linkage strategies that can be used, so long as they are cleavable in the intended environment, include crosslinking and chemical modification using primary amines (—$NH_2$), carboxyls (—COOH), and carbonyls (—CHO).

As discussed below, this approach can be chemically compatible with a broad range of other bioactive components. Further, other known chemical linkage strategies could be utilized to conjugate a broad range of chemicals/drugs to CMC, including small molecule drugs, peptide and protein drugs. These drugs can be linked to a CMC substrate singly or in combinations, and in the presence or absence of one or more targeting molecules.

Example 6

Figure 38:
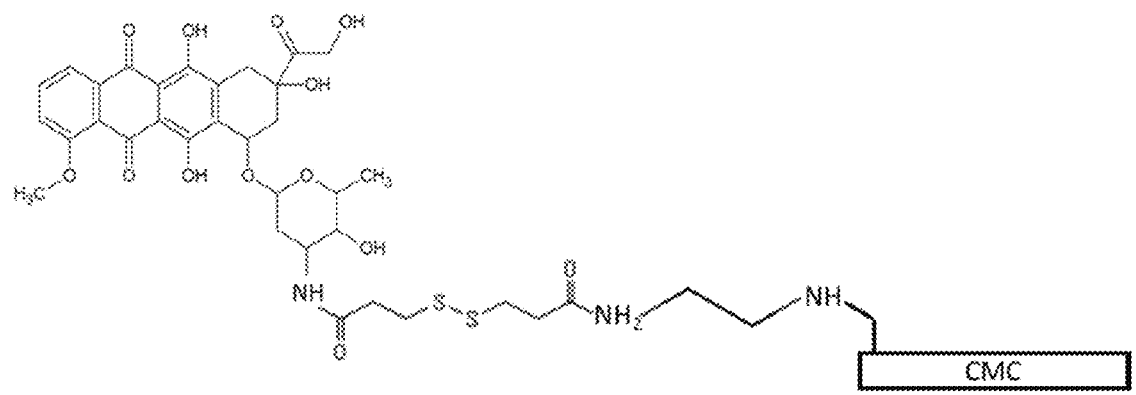
FIG. 38 shows a chemical schematic of the Doxorubicin-S—S-CMC construct.

In this example, Doxorubicin is chemically linked to carboxymethylcellulose (CMC) through a cleavable disulfide bond. The synthesis strategy employed creates a sulfhydryl-bridged doxorubicin-CMC complex that is cleavable (i.e., able to release the drug) in a reductive environment such as cytosol and other cell-compartments, the extracellular space of the tumor microenvironment, or reducing environments created by cellular stress (redox). Further, the release of doxorubicin could also be triggered by targeted introduction of reducing agent such as dithiothreitol (DTT), beta-mercaptoethanol (MEA), Tris(2-carboxyethyl)phosphine hydrochloride (TCEP) or others, together with or subsequent to drug delivery. FIG. 38 shows a chemical schematic of the Doxorubicin-S—S-CMC construct.

In this example the synthesis process is composed of 3 major steps:

1) Highly purified Doxorubicin-SH preparation by 3' amin-conversion to sulfhydryl-group.
2) Amination of free HO-groups on dextrose units of CMC.
3) Crosslinking of Doxorubicin-SH to $NH_2$-CMC Detailed approaches for achieving the three above steps are provided below.

(1) Highly Purified Doxorubicin-SH Preparation by 3' Amin-Conversion to Sulfhydryl-Group.

The process relies on linking doxorubicin to a solid support through sulfhydryl-bridge formation. After complete removal of the residual reactants the doxorubicin-SH is cleaved off of the support and released using a reductive agent (e.g., MEA). The eluted doxorubicin-SH is vacuum dried to remove the reducing agent and stored at −20° C. or reconstructed for further use. The described process ensures that only pure modified sulfhydryl-doxorubicin is recovered as final product.

Figure 39:
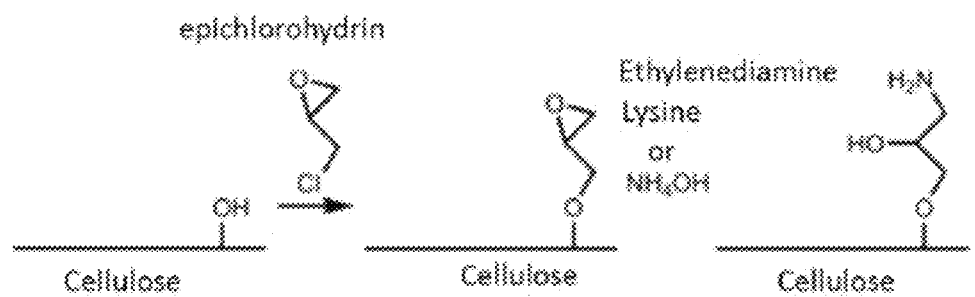
FIG. 39 is a schematic of preparing of $NH_2$-cellulose for solid support using epichlorohdrin and ammonium hydroxide.

Methods:

a. Preparation of $NH_2$-Cellulose for Solid Support Using Epichlorohdrin and Ammonium Hydroxide FIG. 39 shows a two-step ammination of cellulose in alkaline environment using epichlorohydrinand ammonium hydroxide.

Figure 40:
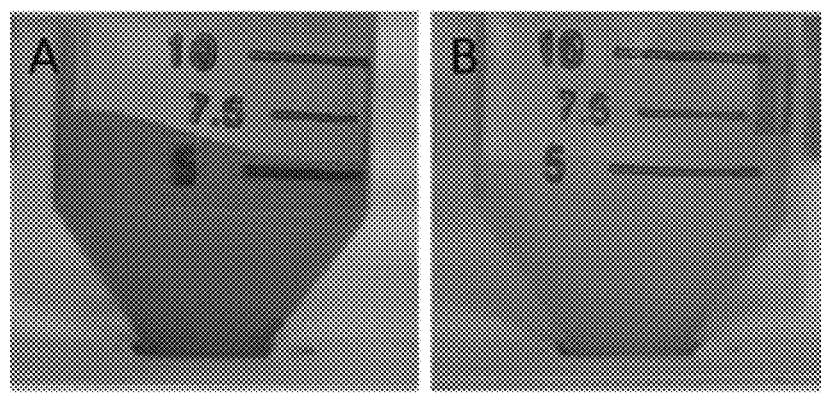
FIG. 40 shows Doxorubicin S—S cross-linked to cellulose support.

Rehydrate 25 g cellulose particles in 200 ml 2n NaOH.
With continuous stirring bring it to 60° C.
When the cellulose suspension reached 60° C. 1.5 g of epichlorohdrin per g cellulose is added.
Vigorously stir at 60° C. for 2 hours.
Wash the epoxide-cellulose 4× with 500 ml distilled water to obtain pH 7-8.
Resuspend epoxide-cellulose particles in 200 ml 0.1n NaOH.
With continuous stirring bring it to 60° C.
When the epoxide-cellulose suspension reached 60° C., 150 ml cc$NH_4$—OH is added.
Vigorously stir at 60° C. for 2 hours.
Wash the aminated-cellulose 4× with 500 ml distilled water to obtain pH ~7.
Store at 4° C. until used in (b) doxorubicin/$NH_2$-cellulose crosslinking reaction.

b. Crosslinking Doxorubicin to Aminated-Cellulose Using Internally Cleavable Dithiobis[Succinimidyl Propionate] (DSP) Adapter FIG. 40 shows Doxorubicin S—S cross-linked to cellulose support, A: Doxorubicin-S—S-cellulose after 4 cycles of washing, B: Aminated-cellulose with no doxorubicin binding from the sham reaction after 4 washing cycles.

Prepare 1 g $NH_2$-cellulose in 10 ml PBS
Prepare 8 ml doxorubicin solution in water at 1 mg/ml
Prepare 80 mg DSP in 2 ml dry DMSO
Mix all 3 reagents and incubate at RT for 30 min
Prepare sham reaction with DMSO only, no DSP.
Wash doxorubicin-S—S-cellulose conjugate 4× with 50 ml water pH adjusted to 5 to remove unbound doxorubicin and other residual reactants.
After final wash resuspend cleaned doxorubicin-cellulose in 10 ml PBS, store at 4° C. until desired cleavage of the S—S bonds and release of the doxorubicin-SH.

c. Elution and Purification of Clean Doxorubicin-SH from Cellulose Support

Figure 41:
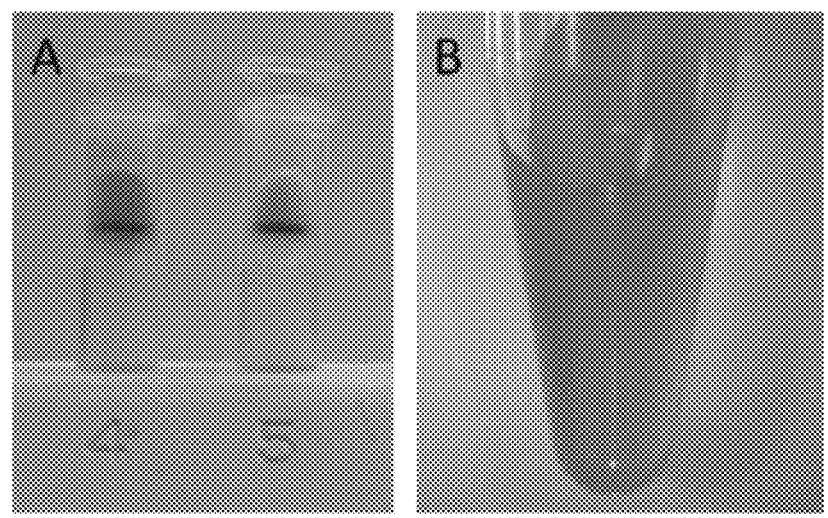
FIG. 41 shows Doxorubicin-S—S-cellulose and cellulose sample from sham reaction prepared for cleavage and elution in a column.

FIG. 41 shows Doxorubicin-S—S-cellulose (#4) and cellulose sample from sham reaction (#5) prepared for cleavage and elution in a column (A). The doxorubicin-SH (B) after elution was further purified by vacuum-drying and reconstructed in water.

One ml samples of doxorubicin-S—S-cellulose slurry (FIG. 40A) and the sham control (FIG. 40B) were packed in chromatography-columns (FIG. 41A).
Columns were washed with 1 ml distilled water.
To cleave and elute the doxorubicin-SH 0.5 ml of 0.1 M 2-mercaptoethanol was added.
Columns were incubated at 37° C. for 30 min and then eluted.
The elution was repeated with an additional 0.5 ml 0.1 M 2-mercaptoethanol.
The collected doxorubicin-SH was vacuum dried.
Dried doxorubicin-SH was stored at −20° C. desiccated or reconstructed in $H_2O$ for further use (FIG. 41B).

(2) Amination of Free HO-Groups on Dextrose Units of CMC.

The basic reactions of the amination of CMC are performed as described above but in solution. Therefore the residual reactants are removed by repeated precipitation with ethanol since CMC is generally insoluble in organic solvents.

Figure 42:
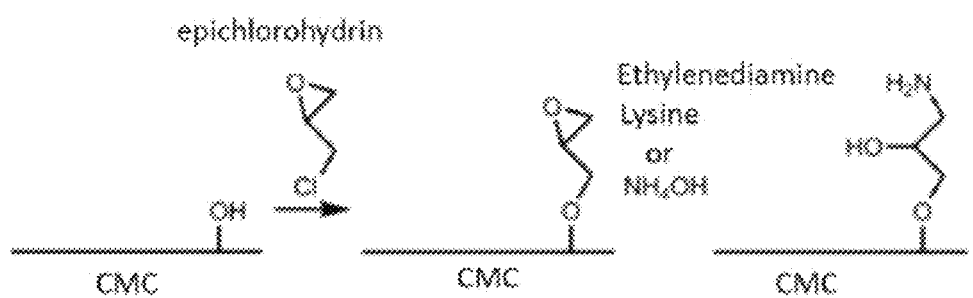
FIG. 42 shows a two-step ammination of CMC in alkaline environment using epichlorohydrinand ammonium hydroxide.

FIG. 42 shows a two-step ammination of CMC in alkaline environment using epichlorohydrinand ammonium hydroxide.

Methods:
a. Prepare 5% CMC in $H_2O$
dissolve 20 g in 400 ml
On a heating/stirring plate bring it to 60° C.
Move it to an oven equipped with a stirring plate and set to 60° C.
Stir 0/N, completely dissolve CMC.

b. $NH_2$-CMC Preparation Using Epichlorohdrin and Ammonium Hydroxide.

To 200 ml 5% CMC solution add NaOH to bring it to final concentration of 2.5 n.
With continuous stirring bring it to 60° C.
When the CMC solution reaches 60° C. 1.5 g, epichlorohdrin per g CMC is added
Vigorously stir at 60° C. for 2 hours.
Add epichlorohydrin (18 mmol/g CMC that is 1.66 g/g CMC or 1.4 ml/g CMC).
Temperature will rise to 65–70° C., let it cool down to 60° C.
Reaction time is 2 h from the addition of epichlorohydrin.
Precipitate Epoxide-CMC w/EtOH by adding 4 vol. (80% final conc.) 0/N at 4° C.
Centrifuge at 2K rpm for 20 min, decant, air-dry briefly.
Resolve Epoxide-CMC in 200 ml 0.1n NaOH
On a heating/stirring plate bring it to 60° C.
Add 150 ml cc$NH_4$—OH (29% w/v)
React for 2 h at 60° C.
Precipitate as in steps above.
Wash pelleted $NH_2$-CMC w/90% EtOH twice.
Resolubilize in 100 ml $H_2O$ (get it in solution completely).
Repeat precipitation step as before.
Reconstruct in 100 ml $H_2O$.
Neutralize the residual NaOH and $NH_4$—OH with 4 n HCl, get ~pH 6.5-8.5 range.
Test for recovery efficiency of $NH_2$-CMC. (Expected is 60-80%)

3) Cross-Linking of Doxorubicin-SH to $NH_2$-CMC.

The cross-linking of Doxorubicin-SH to $NH_2$-CMC utilizes a hetero-bi-functional adapter (N-Succinimidyl 3-(2-pyridyldithio)-propionate (SPDP)) to achieve a short extension at the 3'-$NH_2$ of the doxorubicin upon release from the doxorubicin-S—S-CMC conjugate preserving the functionality of doxorubicin.

Methods:
Prepare 1 g $NH_2$-CMC in 10 ml PBS
Prepare 5 ml doxorubicin-SH solution in water at 0.5 mg/ml
Prepare 40 mg SPDP in 1 ml dry DMSO
Mix all 3 reagents and incubate at RT for 30 min
Prepare sham reaction with DMSO only, no SPDS.
Precipitate doxorubicin-S—S-CMC conjugate 4× volume of ethanol pH adjusted to 5 with 1 n HCl to remove unbound doxorubicin and other residual reactants.
Resolve pelleted doxorubicin-S—S-CMC in 10 ml water.
Dialyze doxorubicin-S—S-CMC solution using spectrapore dialysis tubing (MW cutoff 3,500 dalton) against 21 distilled water changing the distilled water 2× in every 12 hours at 4° C.
Precipitate doxorubicin-S—S-CMC as above with ethanol
Vacuum dry pelleted doxorubicin-S—S-CMC.
Store at −20° C. until use or reconstruct at the required concentration with water.

Conjugation and release were validated by quantification of the active epoxide group using titration according to equation:

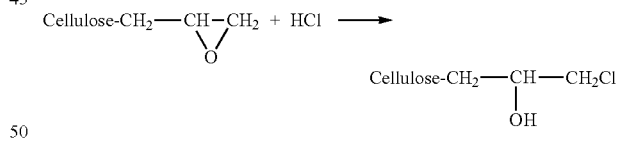

Other Linkable Bioactive Components

Although Doxorubicin is the bioactive component in the above-disclosed embodiment, other bioactive components can be used and be linked to a CMC or other biocompatible structural substrate. Bioactive components suitable for use include other cytotoxic agents traditionally used to treat cancer. Such agents may include, but are not limited to, alkylating agents such as busulfan, hexamethylmelamine, thiotepa, cyclophosphamide (Cytotaxan), mechlorethamine, uramustine, melphalan, chlorambucil, carmustine, streptozocin, dacarbazine, temozolomide, ifosfamide, and the like; anti-metabolites such as methotrexate, azathioprine, mercaptopurine, fludarabine, 5-fluorouracial, and the like; anthracyclines such as daunorubicin, epirubicin, idarubicin, mitoxantrone, and the like; plant alkaloids and terpenoids such as vincristine, vinblastine, vinorelbine, vindesine, podophyllotoxin, paclitaxel, doclitaxel, and the like; topoisomerase inhibitors such as irinotecan, amsacrine, topotecan, etoposide, teniposide, and the like; antibody agents, such as rituximab, trastuzumab, bevacizumab, erlotinib, dactinomycin; finasteride; aromatase inhibitors; tamoxifen; goserelin; imatinib mesylate.

Other suitable compounds that can be the bioactive components used herein include, for instance, proteinaceous compounds, such as insulin, peptide antimicrobials (e.g., naturally occurring defensins, cathelicidins and other proteins with anti-bacterial and/or antiviral activity and synthetic derivatives of naturally occurring peptide antimicrobials including truncated or structurally modified variants), immunoglobulins (e.g., IgG, IgM, IgA, IgE), TNF-α, antiviral medications, etc.; polynucleotide agents, such as plasmids, siRNA, RNAi, nucleoside anticancer drugs, vaccines, etc.; small molecule agents, such as alkaloids, glycosides, phenols, etc.; anti-infection agents, hormones, drugs regulating cardiac action or blood flow, pain control; and so forth. Suitable compounds also include electrophilic nitro-fatty acids ($FA-NO_2$) such as nitro-oleic acid ($OA-NO_2$) and nitro-linoleic acid ($LN-NO_2$) and their derivatives. Suitable compounds also include redox cycling nitroxides such as TEMPOL, as well as targeted derivatives such JP4-039 and the related family of compounds, and XJB-5-131 and the related family of compounds. Suitable compounds also include the transcription factor XBP1, its derivative XBP1s, and synthetic derivatives of XBP1 including XBP1 pathway stimulating factors. Suitable compounds also include neurokin 1 receptor (NK1R) agonists including tachykinins (e.g. substance P) and NKR1 such as aprepitant (Emend), their derivatives. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, non-steroid anti-inflammatory agents, oligosaccharides, parathyroid hormone and analogs, parathyroid hormone antagonists, prostaglandin antagonists, prostaglandins, scopolamine, sedatives, serotonin agonists and antagonists, tissue plasminogen activators, tranquilizers, vaccines with or without carriers/adjuvants, vasodilators, major diagnostics such as tuberculin and other hypersensitivity agents. Vaccine formulations may include an antigen or antigenic composition capable of eliciting an immune response against a human pathogen or from other viral pathogens.

Doxorubicin in Combination with Other Bioactive Components

In addition, as discussed in more detail below, each of the above bioactive components can be integrated into a biocompatible material in combination with doxorubicin. Thus, for example, doxorubicin can be used in combination with any of the other cytotoxic agents listed above (e.g., doxorubicin+cyclophosphamide, doxorubicin+5-fluorouracial, and so on) for using the delivery systems disclosed herein. When used in combination with doxorubicin, both the doxorubicin and the other bioactive component can be linked to the CMC or other biocompatible structure. In another embodiment, one of the two components (either doxorubicin or the other bioactive component) can be linked to the CMC or other biocompatible structural substrate as discussed herein and the second component (the remaining component) can be mixed (i.e., not generally chemically linked to the CMC or other biocompatible structure) into the biocompatible structure. In a third embodiment, as discussed elsewhere herein, both the doxorubicin and other bioactive component can be freely integrated into the biocompatible structure.

In addition, as discussed in detail above, dissolvable microneedle arrays can also include doxorubicin in combination with each of the other bioactive agents described herein, including, for example, immunostimulants such as Poly(I:C). For example, as described herein, doxorubicin alone, Poly(I:C) alone, or doxorubicin and Poly(I:C) can be incorporated into the same MNA.

Linkage Strategies for Use with Bioactive Components and Substrates

In some embodiments, a linkage between the bioactive component(s) and the substrate can be provided by a linker that is selected from the group consisting of a hydrazine group, a polypeptide, a disulfide group, and a thioether group.

As used herein, "linker" refers to a moiety that connects a first region of the bioactive component to a second region of a biocompatible material through chemical bonds (directly or indirectly). As described herein, the connection can be severed so as to release a biologically active form of the bioactive component. An example of a linker is a moiety that comprises a bond that is stable at neutral pH but is readily cleaved under conditions of low pH. Some linkers described herein can be moieties that comprise a bond that is stable at pH values between 7 and 8 but is readily cleaved at pH values between 4 and 6. Another example of a linker is a moiety that comprises a bond that is readily cleaved in the presence of an enzyme. Preferred examples of such enzyme-sensitive linkers are peptides comprising a recognition sequence for an endosomal peptidase. Another example of a linker is a redox potential-sensitive linker that is stable under conditions of low reduction potential (e.g., low thiol or glutathione concentration) but cleaved under conditions of high reduction potential (e.g., high thiol or glutathione concentration). Preferred examples of such redox potential-sensitive linkers include disulfides and sulfenamides. Particularly preferred examples include substituted aryl-alkyl disulfides in which the aryl group is substituted with sterically-demanding and electron-withdrawing or electron-donating substitutents, so as to control the sensitivity of the disulfide linkage towards reaction with thiol. Another example of a linker is a moiety that comprises a bond that is readily cleaved upon exposure to radiation. Examples of such radiation-sensitive linkers are 2-nitrobenzyl ethers that are cleaved upon exposure to light. Particularly preferred examples of linkers are moieties that mask the biological activity of one of the two linked molecules until the linkage is severed.

In some embodiments, the linkage can be cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells. Most typical are peptidyl linkers that are cleavable by enzymes that are present in targeted cells or tissues. For example, a peptidyl linker that is cleavable by the thiol-dependent protease cathepsin-B, which is highly expressed in cancerous tissue, can be used (e.g., a Phe-Leu or a Gly-Phe-Leu-Gly) linker). Other such linkers are described, e.g., in U.S. Pat. No. 6,214,345. In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In some embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT. See, e.g., U.S. Pat. No. 4,880, 935.

In view of the many possible embodiments to which the principles of the disclosed embodiments may be applied, it should be recognized that the illustrated embodiments are only preferred examples and should not be taken as limiting the scope of protection. Rather, the scope of the protection is defined by the following claims. We therefore claim all that comes within the scope and spirit of these claims.

We claim:

1. A dissolvable microneedle array for transdermal insertion into a patient comprising:
    a substrate comprising a biocompatible material that forms base portion and a plurality of microneedles extending from the base portion; and
    one or more bioactive components conjugated to the biocompatible material,
    wherein the one or more bioactive components are cleavable in vivo by an enzyme to release the bioactive component from the biocompatible material, or the bioactive component retains function when conjugated to the biocompatible material.

2. The microneedle array of claim 1, wherein the biocompatible material is carboxymethylcellulose.

3. The microneedle array of claim 1, wherein the one or more bioactive components are bonded to the biocompatible material by a disulfide bond.

4. The microneedle array of claim 1, wherein the one or more bioactive components are cleavable in vivo in response to pH, temperature, or both.

5. The microneedle array of claim 1, wherein the one or more bioactive components comprise Doxorubicin.

6. The microneedle array of claim 5, wherein the amount of Doxorubicin ranges from about 1 to 1000 µg for chemotherapy.

7. The microneedle array of claim 1, wherein the one or more bioactive components are in a higher concentration in the plurality of microneedles than in the base portion.

8. The microneedle array of claim 7, wherein substantially all of the one or more bioactive components are located in the plurality of microneedles so that the base portion is substantially formed without any bioactive components contained therein, the one or more bioactive components are locally concentrated in the plurality of microneedles so that the one or more bioactive components are generally present only in an upper half of respective microneedles in the microneedle array, and each microneedle comprises a plurality of layers of the biocompatible material.

9. The microneedle array of claim 1, wherein the one or more bioactive components comprise at least two different bioactive components conjugated to the biocompatible material.

10. The microneedle array of claim 9, wherein the at least two different bioactive components are selected from the group consisting of a chemotherapeutic agent, an adjuvant, and a chemo attractant for a cancer chemo immunotherapy application.

11. The microneedle array of claim 9, wherein the bioactive component comprises an antigen and an adjuvant for a vaccine application.

12. The microneedle array of claim 1, wherein the one or more bioactive component comprises at least one viral vector.

13. The microneedle array of claim 12, wherein the at least one viral vector comprises an adenovector.

14. A dissolvable microneedle array for transdermal insertion into a patient comprising:
    a substrate comprising a biocompatible material that forms base portion and a plurality of microneedles extending from the base portion; and
    a first bioactive component conjugated to the biocompatible material, the bioactive component being Doxorubicin,
    wherein the first bioactive component is cleavable in vivo by an enzyme to release the first bioactive component from the biocompatible material, or the first bioactive component retains function when conjugated to the biocompatible material.

15. The microneedle array of claim 14, wherein the biocompatible material is carboxymethylcellulose.

16. The microneedle array of claim 14, wherein the first bioactive component is bonded to the biocompatible material by a disulfide bond.

17. The microneedle array of claim 14, wherein the first bioactive components is cleavable in vivo in response to pH, temperature, or both.

18. The microneedle array of claim 14, wherein the amount of Doxorubicin ranges from about 1 to 1000 µg for chemotherapy.

19. The microneedle array of claim 14, further comprising a second bioactive component.

20. The microneedle array of claim 19, wherein the second bioactive component is selected from the group consisting of Poly-IC or Poly-ICLC.

21. The microneedle array of claim 19, wherein the second bioactive component is also conjugated to the biocompatible material.

22. The microneedle array of claim 19, wherein the second bioactive component is mixed into the biocompatible material.

23. A dissolvable microneedle array for transdermal insertion into a patient comprising:
- a substrate comprising a biocompatible material that forms base portion and a plurality of microneedles extending from the base portion; and
- one or more bioactive components conjugated to the biocompatible material,
- wherein the one or more bioactive components are cleavable in vivo to release the bioactive component from the biocompatible material, or the bioactive component retains function when conjugated to the biocompatible material, and
- wherein the one or more bioactive components are bonded to the biocompatible material by a disulfide bond which is cleavable in vivo by an enzyme.

24. The microneedle array of claim 23, wherein the one or more bioactive components are covalently bonded to the biocompatible material.

25. The microneedle array of claim 23, wherein the one or more bioactive components are bonded to the biocompatible material by a disulfide bond.

26. The microneedle array of claim 23, wherein the biocompatible material is carboxymethylcellulose.

27. The microneedle array of claim 23, wherein the one or more bioactive components comprise Doxorubicin.

28. The microneedle array of claim 27, wherein the amount of Doxorubicin ranges from about 1 to 1000 µg for chemotherapy.

29. The microneedle array of claim 23, wherein the one or more bioactive components are in a higher concentration in the plurality of microneedles than in the base portion.

30. The microneedle array of claim 29, wherein substantially all of the one or more bioactive components are located in the plurality of microneedles so that the base portion is substantially formed without any bioactive components contained therein, the one or more bioactive components are locally concentrated in the plurality of microneedles so that the one or more bioactive components are generally present only in an upper half of respective microneedles in the microneedle array, and each microneedle comprises a plurality of layers of the biocompatible material.

31. The microneedle array of claim 23, wherein the one or more bioactive components comprise at least two different bioactive components conjugated to the biocompatible material.

32. The microneedle array of claim 31, wherein the at least two different bioactive components are selected from the group consisting of a chemotherapeutic agent, an adjuvant, and a chemo attractant for a cancer chemo immunotherapy application.

33. The microneedle array of claim 31, wherein the bioactive component comprises an antigen and an adjuvant for a vaccine application.

34. The microneedle array of claim 23, wherein the one or more bioactive component comprises at least one viral vector.

35. The microneedle array of claim 34, wherein the at least one viral vector comprises an adenovector.

36. A dissolvable microneedle array for transdermal insertion into a patient comprising:
- a substrate comprising a biocompatible material that forms base portion and a plurality of microneedles extending from the base portion; and
- one or more bioactive components conjugated to the biocompatible material,
- wherein the one or more bioactive components are cleavable in vivo by an enzyme to release the bioactive component from the biocompatible material, or the bioactive component retains function when conjugated to the biocompatible material, and
- wherein the one or more bioactive component comprises at least one viral vector wherein the bioactive component is bonded to the biocompatible material by a disulfide bond which is cleavable in vivo by an enzyme.

37. The microneedle array of claim 36, wherein the one or more bioactive components are covalently bonded to the biocompatible material.

38. The microneedle array of claim 36, wherein the one or more bioactive components are bonded to the biocompatible material by a disulfide bond.

39. The microneedle array of claim 36, wherein the biocompatible material is carboxymethylcellulose.

40. The microneedle array of claim 36, wherein the one or more bioactive components are cleavable in vivo in response to pH, temperature, or both.

41. The microneedle array of claim 36, wherein the one or more bioactive components are in a higher concentration in the plurality of microneedles than in the base portion.

42. The microneedle array of claim 41, wherein substantially all of the one or more bioactive components are located in the plurality of microneedles so that the base portion is substantially formed without any bioactive components contained therein, the one or more bioactive components are locally concentrated in the plurality of microneedles so that the one or more bioactive components are generally present only in an upper half of respective microneedles in the microneedle array, and each microneedle comprises a plurality of layers of the biocompatible material.

43. The microneedle array of claim 36, wherein the one or more bioactive components comprise at least two different bioactive components conjugated to the biocompatible material.

44. The microneedle array of claim 43, wherein the bioactive component comprises an antigen and an adjuvant for a vaccine application.

45. The microneedle array of claim 36, wherein the at least one viral vector comprises an adenovector.

46. A dissolvable microneedle array for transdermal insertion into a patient comprising:
- a substrate comprising a biocompatible material that forms base portion and a plurality of microneedles extending from the base portion; and
- one or more bioactive components conjugated to the biocompatible material,
- wherein the one or more bioactive components are cleavable in vivo to release the bioactive component from the biocompatible material, or the bioactive component retains function when conjugated to the biocompatible material,
- wherein the one or more bioactive components comprise at least two different bioactive components conjugated to the biocompatible material, and
- wherein the bioactive component comprises an antigen and an adjuvant for a vaccine application.

47. The microneedle array of claim 46, wherein the one or more bioactive components are covalently bonded to the biocompatible material.

48. The microneedle array of claim 46, wherein the one or more bioactive components are bonded to the biocompatible material by a disulfide bond.

49. The microneedle array of claim 46, wherein the biocompatible material is carboxymethylcellulose.

50. The microneedle array of claim 46, wherein the one or more bioactive components are cleavable in vivo by an enzyme.

51. The microneedle array of claim 46, wherein the one or more bioactive components are cleavable in vivo in response to pH, temperature, or both.

52. The microneedle array of claim 46, wherein the one or more bioactive components further comprise Doxorubicin.

53. The microneedle array of claim 52, wherein the amount of Doxorubicin ranges from about 1 to 1000 µg for chemotherapy.

54. The microneedle array of claim 46, wherein the one or more bioactive components are in a higher concentration in the plurality of microneedles than in the base portion.

55. The microneedle array of claim 54, wherein substantially all of the one or more bioactive components are located in the plurality of microneedles so that the base portion is substantially formed without any bioactive components contained therein, the one or more bioactive components are locally concentrated in the plurality of microneedles so that the one or more bioactive components are generally present only in an upper half of respective microneedles in the microneedle array, and each microneedle comprises a plurality of layers of the biocompatible material.

56. The microneedle array of claim 46, wherein the one or more bioactive component further comprises at least one viral vector.

57. The microneedle array of claim 56, wherein the at least one viral vector comprises an adenovector.

58. A dissolvable microneedle array for transdermal insertion into a patient comprising:
 a substrate comprising a biocompatible material that forms base portion and a plurality of microneedles extending from the base portion; and
 a first bioactive component conjugated to the biocompatible material, the bioactive component being Doxorubicin,
 wherein the first bioactive component is cleavable in vivo to release the first bioactive component from the biocompatible material, or the first bioactive component retains function when conjugated to the biocompatible material, and
 wherein the second bioactive component is mixed into the biocompatible material wherein the bioactive components are bonded to the biocompatible material by a disulfide bond which is cleavable in vivo by an enzyme.

59. The microneedle array of claim 58, wherein the first bioactive component is covalently bonded to the biocompatible material.

60. The microneedle array of claim 58, wherein the first bioactive component is bonded to the biocompatible material by a disulfide bond.

61. The microneedle array of claim 58, wherein the biocompatible material is carboxymethylcellulose.

62. The microneedle array of claim 58, wherein the first bioactive components is cleavable in vivo in response to pH, temperature, or both.

63. The microneedle array of claim 58, wherein the amount of Doxorubicin ranges from about 1 to 1000 µg for chemotherapy.

64. The microneedle array of claim 58, wherein the second bioactive component is selected from the group consisting of Poly-IC or Poly-ICLC.

* * * * *